US008655429B2

(12) United States Patent
Kuduvalli et al.

(10) Patent No.: US 8,655,429 B2
(45) Date of Patent: Feb. 18, 2014

(54) ROBOTIC ARM FOR A RADIATION TREATMENT SYSTEM

(75) Inventors: Gopinath R. Kuduvalli, San Jose, CA (US); Sohail Sayeh, San Ramon, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1716 days.

(21) Appl. No.: 11/824,080

(22) Filed: Jun. 29, 2007

(65) Prior Publication Data

US 2009/0003975 A1    Jan. 1, 2009

(51) Int. Cl.
*A61B 5/05* (2006.01)

(52) U.S. Cl.
USPC ............... 600/407; 250/492.1; 250/522.1; 250/491.1

(58) Field of Classification Search
None
See application file for complete search history.

(56) References Cited

U.S. PATENT DOCUMENTS

| | | | | | |
|---|---|---|---|---|---|
| 1,019,105 | A | * | 3/1912 | Waters | 451/194 |
| 1,182,365 | A | * | 5/1916 | Goldberg et al. | 56/199 |
| 1,201,274 | A | * | 10/1916 | Denquer | 5/618 |
| 1,720,052 | A | * | 7/1929 | Norton | 525/508 |
| 2,893,164 | A | * | 7/1959 | Martin | 248/188.2 |
| 2,933,850 | A | * | 4/1960 | Martin | 248/188.2 |
| 4,823,259 | A | * | 4/1989 | Perzley et al. | 700/251 |
| 4,864,966 | A | * | 9/1989 | Anderson et al. | 427/265 |
| 5,060,533 | A | * | 10/1991 | Torii et al. | 74/490.05 |
| 5,408,409 | A | * | 4/1995 | Glassman et al. | 600/407 |
| 5,430,643 | A | * | 7/1995 | Seraji | 700/263 |
| 6,033,415 | A | * | 3/2000 | Mittelstadt et al. | 606/130 |
| 7,154,991 | B2 | * | 12/2006 | Earnst et al. | 378/65 |
| 7,166,852 | B2 | * | 1/2007 | Saracen et al. | 250/491.1 |
| 7,831,073 | B2 | * | 11/2010 | Fu et al. | 382/128 |
| 7,853,308 | B2 | * | 12/2010 | Sauer et al. | 600/425 |
| 2002/0029419 | A1 | * | 3/2002 | Weil et al. | 5/601 |
| 2003/0023346 | A1 | * | 1/2003 | Salisbury et al. | 700/245 |
| 2005/0028279 | A1 | * | 2/2005 | de Mooy | 5/601 |
| 2005/0180544 | A1 | * | 8/2005 | Sauer et al. | 378/195 |
| 2005/0234327 | A1 | * | 10/2005 | Saracen et al. | 600/407 |
| 2006/0004281 | A1 | * | 1/2006 | Saracen | 600/414 |
| 2006/0074299 | A1 | * | 4/2006 | Sayeh | 600/426 |
| 2006/0074304 | A1 | * | 4/2006 | Sayeh | 600/427 |
| 2007/0003123 | A1 | * | 1/2007 | Fu et al. | 382/131 |
| 2007/0016174 | A1 | * | 1/2007 | Millman et al. | 606/1 |
| 2007/0169265 | A1 | * | 7/2007 | Saracen et al. | 5/601 |
| 2007/0248214 | A1 | * | 10/2007 | Smith | 378/109 |
| 2009/0003532 | A1 | * | 1/2009 | Weber | 378/209 |

FOREIGN PATENT DOCUMENTS

JP         07171779 A  *  7/1995  ............... B25J 9/10
WO       WO94/13205 A1     6/1994

OTHER PUBLICATIONS

Coste-Maniere, E., "Robotic whole body stereotactic radiosurgery: clinical advantages of the CyberKnife® integrated system", The International Journal of Medical Robotics +Computer Assisted Surgery, 2005, www. roboticpublications.com, 14 pages.*
International Search Report and Written Opinion, PCT/US08/04881 filed Apr. 15, 2008, mailed Aug. 6, 2008.

(Continued)

*Primary Examiner* — Andrew Smyth
(74) *Attorney, Agent, or Firm* — Lowenstein Sandler LLP

(57) ABSTRACT

A robotic treatment delivery system including a linear accelerator (LINAC), and a robotic arm coupled to the LINAC. The robotic arm is configured to move the LINAC along at least four rotational degrees of freedom and one substantially linear degree of freedom.

53 Claims, 19 Drawing Sheets

(56) References Cited

OTHER PUBLICATIONS

Supplementary European Search Report, Application No. 08742932.0, dated Oct. 19, 2010, 5 pages.

Examination Report mailed Aug. 4, 2011, for European Patent Application No. 08742932.0, 4 pages.

* cited by examiner

ROBOTIC ARM FOR A RADIATION TREATMENT SYSTEM

TECHNICAL FIELD

Embodiments of the present invention pertain to the field of robotic arms used in radiosurgery.

BACKGROUND

Conventional robots are designed to do exactly the same thing over and over again, such as in an assembly line for assembly. These robots are programmed and configured to repeat a given motion to perform a specific function. Robots are often implemented to perform a lot of functions, more efficiently, and often more precisely than humans.

Conventional robots, typically, include one or two robotic arms. These robotic arms can have multiple segments that help facilitate movement in differing degrees of freedom (DOF). Some conventional robots employ a computer to control the segments of the robotic arm by activating rotation of individual step motors connected to corresponding segments. Other designs may use hydraulics or pneumatics to actuate movement in the arm segments. Computers allow precise, repeatable movements of the robotic arm.

Prior Selectively Compliant Articulated Robot Arm (SCARA) robots operate with 4 or fewer degrees of freedom ("DOF"). In other words, these robotic arms are designed to move along 4 or fewer axes. A typical application for a conventional robotic arm is that of pick-and-place type machine. Pick-and-place type machines are used for automation assembly, automation placing, printed circuit board manufacturing, integrated circuit pick and placing, and other automation jobs that contain small items, such as machining, measuring, testing, and welding. These robotic arms include an end-effector, also known as robotic peripheral, robotic accessory, robot or robotic tool, end of arm (EOA) tooling, or end-of-arm device. The end-effector may be an implement such as a robotic gripper, press tool, paint gun, blowtorch, deburring tool, arc welding gun, drills, etc. These end-effectors are typically placed at the end of the robotic arm and are used for uses as described above. One common end-effector is a simplified version of the hand, which can grasp and carry different objects. Such end effectors typically support maximum payloads ranging from 3 kg-20 kg (6.61-44.09 pounds).

Another type of robot that has been implemented in positioning of a radiation source of a radiation treatment system includes an articulated robotic arm for positioning a radiation source, such as a linear accelerator (LINAC), mounted at a distal end of the articulated robotic arm, for selectively emitting radiation, such as described below in FIG. 1A.

FIG. 1A is a schematic block diagram illustrating a conventional treatment delivery system 100. The depicted treatment delivery system 100 includes a radiation source 103, in the form of a linear accelerator (LINAC), and a treatment couch 106, as described above. The treatment delivery system 100 also includes multiple imaging x-ray sources 107 and detectors 108 (e.g., cameras). The two x-ray sources 107 may be nominally aligned to project imaging x-ray beams through a patient from at least two different angular positions (e.g., separated by 90 degrees, 45 degrees, etc.) and aimed through the patient on the treatment couch 106 toward the corresponding detectors 108 or to a single large imager. The x-ray imaging system generates image data representative of one or more real time or near real time images that show the position and orientation of the target in a treatment coordinate frame. The treatment delivery system 100 may be an image-guided, robotic-based radiation treatment system (e.g., for performing radiosurgery) such as the CyberKnife® system developed by Accuray, Inc. of Sunnyvale, Calif.

In the illustrated embodiment, the LINAC 103 is mounted on a robotic arm 102. The LINAC 103 is used to produce a beam of radiation that can be directed to a target. The robotic arm 102 is a highly articulated robotic arm that may have multiple (e.g., 5 or more) rotational degrees of freedom in order to properly position the LINAC 103 to irradiate a target such as a pathological anatomy with a beam delivered from many angles in an operating volume around the patient. The treatment implemented with the treatment delivery system 100 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (monofraction) or in a small number of sessions (hypo-fractionation) as determined during treatment planning. The treatment delivery system 100 delivers radiation beams according to the treatment plan without fixing the patient to a rigid, external frame to register the intra-operative position of the target volume with the position of the target volume during the pre-operative treatment planning phase.

In addition, the treatment delivery system 100 may include a controller 101 that may implement algorithms to register images obtained from the imaging system (e.g., imaging x-ray sources 107 and detectors 108) with pre-operative treatment planning images obtained from a diagnostic imaging system in order to align the patient on the treatment couch 106 within the treatment delivery system 100. Additionally, these images may be used to precisely position the radiation source 103 with respect to the target volume or target. The controller 101 may contain treatment planning and delivery software, which may be responsive to pre-treatment scan data CT (and/or MRI data, PET data, ultrasound scan data, and/or fluoroscopy imaging data) and user input, to generate a treatment plan consisting of a succession of desired beam paths, each having an associated dose rate and duration at each of a fixed set of treatment positions or nodes. In response to the controller's directions, the robotic arm moves and orients the x-ray LINAC 103, successively and sequentially through each of the nodes, while the x-ray LINAC 103 delivers the required dose as directed by the controller 201. The pre-treatment scan data may include, for example, CT scan data, MRI scan data, PET scan data, ultrasound scan data, and/or fluoroscopy imaging data. Prior to performing a treatment on a patient treatment couch 106, the patient's position and orientation within the frame of reference established by imaging system must be adjusted to match the position and orientation that the patient had within the frame of reference of the CT (or MRI or PET or fluoroscopy) scanner that provided the images used for planning the treatment.

The treatment couch 106 may be a conventional treatment table, such as the AXUM® treatment couch developed by Accuray, Inc. of Sunnyvale, Calif.

Another conventional treatment delivery system is a gantry-based (isocentric) intensity modulated radiotherapy (IMRT) system, in which a radiation source 103 (e.g., a LINAC) is mounted on the gantry in such a way that it rotates in a plane corresponding to an axial slice of the patient. Radiation may be delivered from several positions on the circular plane of rotation. Another conventional treatment delivery system is a stereotactic frame system such as the GammaKnife®, available from Elekta of Sweden.

FIG. 1B is a perspective drawing illustrating a workspace of a conventional radiation treatment system 150 including a set of spatial nodes at which to position the radiation source. The radiation treatment system 150 is similar to the radiation treatment system 100 and includes a radiation source 103, detectors 108, imaging sources 108, and a robotic arm 102. The conventional radiation treatment system 150 also includes a treatment couch 106 and a stand 1 10 upon which the treatment couch 106 is disposed.

During radiation treatment, the patient rests on treatment couch 106, which is maneuvered to position a volume of interest ("VOI") containing a target to a preset position or within an operating range accessible to radiation source 103 (e.g., field of view). The robotic arm 102 has multiple (e.g., six) rotational degrees of freedom capable of positioning the radiation source 103 with a finite number of positions and orientations within its operating envelope.

A collection of spatial nodes and associated safe paths interconnecting these spatial nodes is called a "workspace" or "node set". FIG. 1B illustrates a workspace 111, including a number of spatial nodes 112 each represented by a "+" symbol (only a couple are labeled). Multiple different workspaces may be created and defined for different patient work areas. For example, workspace 111 may be spherical (as illustrated) and defined for treating VOIs residing within the head of a patient 904. Alternatively, workspace 111 may have other geometries (e.g., elliptical) and defined for treating VOIs residing within other areas of a patient. Additionally, multiple workspaces 111 may be defined for different portions of a patient, each having different radius or source to axis distances ("SAD"), such as 650 mm and 800 mm. The SAD is the distance between the collimator in the radiation source 103 and the target within the VOI. The SAD defines the surface area of the workspace 111. In one embodiment of an elliptical workspace, the SAD may range from 900 mm to 1000 mm. Other SADs may be used.

Spatial nodes 112 reside on the surface of workspace 111. Spatial nodes 112 represent positions where the radiation source 103 is pre-programmed to stop and delivery a dose of radiation to the VOI within the patient. During delivery of a treatment plan, robotic arm 102 moves radiation source 103 to each and every spatial node 112, where a dose is determined to be delivered, following a predefined path. The predefined path may also include some spatial nodes 112 where no dose needs to be delivered, in order to simplify the motions of the robotic arm.

FIG. 1B illustrates a node set including an exemplary number of spatial nodes 112 (e.g., 100 to 115). The node set may include spatial nodes 112 substantially uniformly distributed over the geometric surface of workspace 111. The node set includes all programmed spatial nodes 112 and provides a workable number of spatial nodes 112 for effectively computing treatment plan solutions for some ailments and associated VOIs. The node set provides a reasonably large number of spatial nodes 112 such that homogeneity and conformality thresholds can be achieved for a large variety of different VOIs, while providing enough vantage points to avoid critical structures within patients. It should be appreciated that the node set may include more or less spatial nodes 112 than is illustrated or discussed. For example, as processing power increases and experience gained creating treatment plans, the average number of spatial nodes 112 may increase with time to provide greater flexibility and higher quality treatment plans.

In addition to being limited in the spatial nodes due to obstructions and mechanical limitations of the conventional robotic arms, the conventional robotic arms can not be used in some treatments, such as posterior treatments due to these obstructions and mechanical limitations. Also, the conventional robotic arms may have complex paths that are calculated during treatment planning. The paths calculated are complex because all the DOF are rotational DOF. In order to position the LINAC in 3D space using only rotational DOF, most or all of the rotational axes need to be rotated to position the LINAC. For example, in order to move the LINAC a certain distance along a single axis in the 3D space, multiple axes may have to be rotated to move the LINAC to the position that is the certain distance on the single axis.

BRIEF DESCRIPTION OF THE DRAWINGS

Embodiments of the present invention are illustrated by way of example, and not by way of limitation, in the figures of the accompanying drawings and in which.

DETAILED DESCRIPTION

Figure 1A:
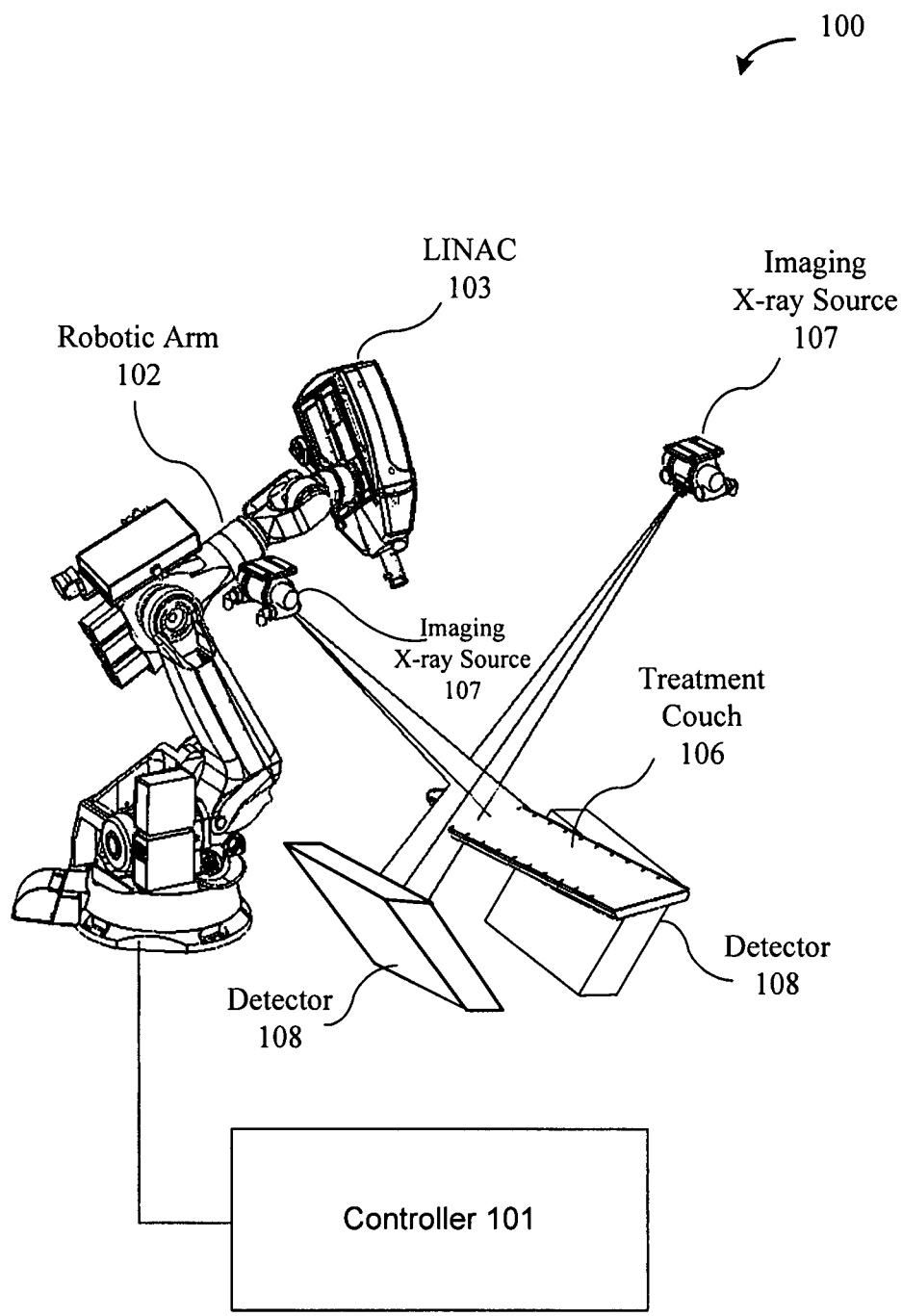
FIG. 1A illustrates a conventional treatment delivery system.

In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

A robotic treatment delivery system is described for adjusting a position and orientation of a radiation source during, for example, therapeutic radiation treatment. The robotic treatment delivery system includes an articulated robotic arm that includes a track mount assembly to facilitate movement of the radiation source in a 3D space, as well raising and lowering the radiation source to high and low positions without compromising the flexibility or positioning in translational and rotational movements. The track mount assembly may be vertically mounted, for example, to a vertical side of a column.

The robotic arm can position a LINAC attached to the robotic arm in five DOF, including one substantially linear DOF. The five DOF may include one rotational axes for translational movements along mutually orthogonal x-, and y-horizontal coordinate axes; three rotational axes for roll-, pitch-, and yaw-rotational movements about x-, y-, and z-axes, respectively; and a substantially vertical, linear axis for translation along a substantially vertical line in a z-coordinate axis perpendicular to the horizontal, x-, and y-coordinate axes or a substantially horizontal, linear axis for translation along a substantially horizontal line in the x- and y-coordinate axes perpendicular to the vertical z-coordinate axis.

In another embodiment, the robotic arm includes an additional rotational DOF including an additional rotational axis for translational movements along the horizontal coordinate axes, totaling six DOF in the robotic arm. The six DOF may include five rotational DOF and one substantially linear DOF. The five rotational DOF may include two rotational axes for translational movements along mutually orthogonal x-, and y-horizontal coordinate axes; three rotational axes for roll-, pitch-, and yaw-rotational movements about x-, y-, and z-axes, respectively. The one substantially linear DOF includes a substantially vertical, linear axis for translation along a substantially vertical line in a z-coordinate axis perpendicular to the horizontal, x-, and y-coordinate axes or a substantially horizontal, linear axis for translation along a substantially horizontal line in the x- and y-coordinate axes perpendicular to the vertical z-coordinate axis.

In another embodiment, the robotic arm includes an additional plate member attached between the shoulder assembly and the track mount assembly to provide an additional rotational DOF, totaling seven DOF in the robotic arm. The seven DOF may include six rotational DOF and one substantially linear DOF. The six DOF include three rotational axes for translational movements along mutually orthogonal x-, y-, and z-coordinate axes; and three rotational axes for roll-, pitch-, and yaw-rotational movements about x-, y-, and z-axes, respectively. The one substantially vertical, linear DOF includes a substantially linear axis for translation along a substantially vertical line in a z-coordinate axis perpendicular to the horizontal, x-, and y-coordinate axes or a substantially horizontal, linear axis for translation along a substantially horizontal line in the x- and y-coordinate axes perpendicular to the vertical z-coordinate axis.

Figure 2A:
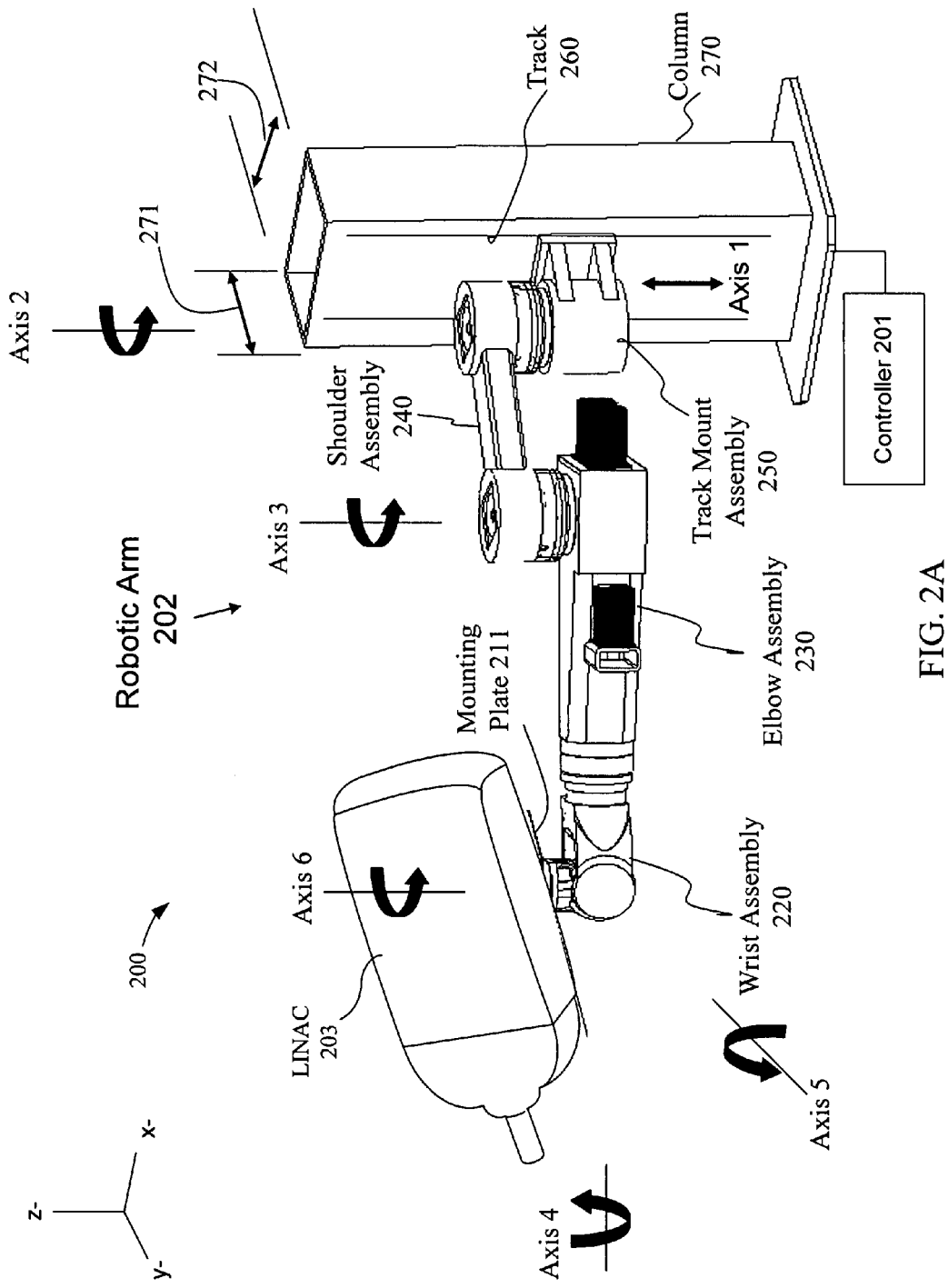
FIG. 2A illustrates one embodiment of a robotic treatment delivery system including a robotic arm having five rotational degrees of freedom and one substantially vertical, linear degree of freedom.

FIG. 2A illustrates one embodiment of a robotic treatment delivery system 200 including a robotic arm having five rotational DOF and one substantially vertical, linear DOF. The robotic treatment delivery system 200 of FIG. 2A includes a robotic arm 202 having a wrist assembly 220, an elbow assembly 230, a shoulder assembly 240, a track mount assembly 250, and a track 260, a LINAC 203, and a column 270. The LINAC 203 may be rotatably attached to the wrist assembly 220, which includes a tool-yaw joint, a tool-pitch joint, and a tool-roll joint. The tool-yaw joint of wrist assembly 220 may be coupled to mounting plate 211, which may be attached to the bottom of the LINAC 203. Alternatively, the tool-yaw joint of wrist assembly 220 may be coupled directly to the bottom of the LINAC 203. The tool-yaw joint of wrist assembly 220 facilitates rotational movement of the LINAC 203 in a yaw-rotation along the z-axis, axis 6 of FIG. 2A. The tool-pitch joint may be coupled to the tool-yaw joint and facilitates rotational movement of the LINAC 203 in a pitch-rotation along the y-axis, axis 5 of FIG. 2A. The tool-roll joints may be coupled to the tool-pitch joint and facilitates rotational movement of the LINAC 203 in a roll-rotation along the x-axis, axis 4 of FIG. 2A.

The elbow assembly 230 may be coupled to the tool-roll joint of wrist assembly 220. The elbow assembly 230 may include three drive shafts and three motors. In one embodiment, the motors discussed herein may be step motors. Alternatively, the motors may be servo motors or other motors known by those of ordinary skill in the art. The first drive shaft may be coupled to the tool-yaw joint and the first motor. The first motor and drive shaft drive rotational movement of LINAC 203 along the yaw axis, axis 6. The second drive shaft may be coupled to the tool-pitch joint and the second motor. The second motor and drive shaft drive rotational movement of the LINAC 203 along the pitch axis, axis 5. The third drive shaft may be coupled to the tool-roll joint and the third motor. The third motor and drive shaft drive rotational movement of the LINAC 203 along the roll axis, axis 4. In one exemplary embodiment, the elbow assembly 230 is ten inches (10") in diameter at the distal end that connects to the tool-roll joint of the wrist assembly 220. Alternatively, the elbow assembly 230 may have a diameter being approximately in a range of three to twenty inches (3"-20"). Alternatively, the elbow assembly 230 may have another shape than circular, for example, rectangular, oval, or other known shapes, and the elbow assembly 230 may have a minimum measurement of its cross section between three (3") to twenty (20") inches.

The shoulder assembly 240 may be coupled to the elbow assembly 230 by an elbow joint and to the track mount assembly 250 by a shoulder joint. The elbow joint includes an elbow gearbox, which may be configured to drive rotational movement of the elbow assembly 230 of the robotic arm 202 in a rotational axis, axis 3 of FIG. 2A. The shoulder joint includes a shoulder gearbox, which may be configured to drive rotational movement of the shoulder assembly 240 of the robotic arm 202 in a rotational axis, axis 2 of FIG. 2A. The elbow and shoulder gearboxes of the shoulder and elbow assemblies 230 and 240 facilitate translational movement of the LINAC 203 in a two-dimensional horizontal plane, for example, in the (x-, y-) plane parallel with the floor. In one embodiment, the elbow and shoulder gearboxes have approximately a two hundred to one gear reduction ratio (200:1). The 200:1 gear reduction ratio of the elbow and shoulder gearboxes may enable support of a load up to five hundred pounds within a deflection error on the LINAC 203, being approximately in a range of zero to sixty millimeters (0 to 60 mm). In one exemplary embodiment, the deflection error 261 is approximately zero to five millimeters (0 to 5 mm). Alternatively, the gear reduction ratios may have a range of approximately ten to one gear reduction ratio (10:1) to approximately six hundred to one gear reduction ratio (600:1). The gear reduction ratio may be selected based on two considerations. First, the gear reduction ratio may allow the use of smaller motors for packaging purposes. Second, the gear reduction ratio may be selected for safety purposes. With a higher gear reduction ratio if all the motors are spinning at a maximum speed, the spinning translates into a reasonable speed of the robotic arm, preventing runaway of the robotic arm. It should be noted that although specific dimensions and gear reduction ratios have been used, other dimensions and gear reduction ratios may be used based on the size and speeds of the desired gearboxes of the robotic arm, for example, the gear reduction ratio may be less than (10:1) and more than (600:1). It should be noted that the structure described herein when referring to supporting a load up to five hundred pounds (500 lbs) may support four times (4×) the weight of the load in order to comply with safety standards. The four times safety factor may be used to ensure that under normal conditions the 1× load does not make the robotic arm buckle or fall over on the patient. Further, although illustrated using a robotic arm having five rotational DOF and one substantially vertical, linear DOF, deflection error applies to the other embodiments of the robotic arm having four, five, or six rotational DOF and one substantially vertical, linear DOF described herein.

In one embodiment, the controller 201, the shoulder and elbow gearboxes of the robotic arm 202, the track mount assembly 250, and the wrist assembly 220, may include components manufactured by KUKA Roboter GmbH of Germany. Alternatively, the controller, the shoulder and elbow gearboxes of the robotic arm 202, the track mount assembly 250, and the wrist assembly 220 may include other types of components.

The track mount assembly 250 may be coupled to a track 260 and to the shoulder joint of the shoulder assembly 240. The track mount assembly 250 and track 260 facilitate translational movement of the LINAC 203 in a substantially vertical, linear axis, axis 1 of FIG. 2A. The substantially vertical, linear axis (z-) may be substantially perpendicular to the two dimensional horizontal plane (x-, y-). In one embodiment, the track may be vertically oriented, for example, vertically mounted to a vertical side of column 270. The column 270 may be secured or mounted to the floor of the treatment room during therapeutic radiation treatment or below the floor in a pit. In another embodiment, column 270 may be secured or mounted to the ceiling of the treatment room during therapeutic radiation treatment. Alternatively, the track 260 may be vertically mounted to other structures known to those skilled in the art, such as a wall, pedestal, block, or base structure. Column 270 includes a column depth 271, and a column width 272. In one embodiment, the column depth 271 is at least approximately ten inches (10") and the column width 272 is at least approximately fifteen inches (15"). In one exemplary embodiment, the column depth 271 is approximately seventeen inches (17") and the column width 272 is approximately twenty-two inches (22"). In one embodiment, the column 270 has at least a principal moment of inertia about the x-axis of approximately 800 $in^4$. In one exemplary embodiment, the principal moment of inertial about the x-axis is approximately 1200 $in^4$. Alternatively, other dimensions may be used.

The above mentioned arrangement of the wrist assembly 220, elbow assembly 230, shoulder assembly 240, track mount assembly 250, and track 260 facilitate the positioning of the LINAC 203 using five rotational DOF and one translational substantially vertical, linear DOF. The five rotational and one translational substantially vertical, linear DOF of the robotic arm 202 of the robotic treatment delivery system 200 may position the LINAC 203 in substantially any place in a desired treatment area, such as a workspace within the mechanical range of motion of the robotic arm 202. The robotic arm 202 may position the LINAC 203 to have a tool center position (TCP) or isocenter in multiple locations within the workspace or treatment area. Alternatively, the robotic arm 202 may be configured to facilitate motion of the LINAC 203 along five rotational DOF and one substantially vertical, linear DOF. In one exemplary embodiment, the five DOF includes two rotational axes for translational movements along mutually orthogonal, horizontal coordinate axes (x-, and y-); and three rotational axes for roll-, pitch-, and yaw-rotational movements about x-, y-, and z-axes, respectively. The one substantially vertical, linear DOF includes a substantially linear axis for translational movement along a substantially vertical line in a coordinate axis (z-) substantially perpendicular to the horizontal coordinate axes (x-, and y-). Alternatively, the substantially linear DOF is a substantially horizontal, linear DOF that includes a substantially linear axis for translational movement along a substantially horizontal line in horizontal coordinate axes (x-, and y-) substantially perpendicular to the vertical coordinate axes (z-).

In one embodiment, the robotic arm 202 includes one or more motion actuators for moving the LINAC 203, in accordance with directions from the controller 201. An interface module may allow the LINAC 203 to interface with a sensor system (not illustrated in FIG. 2A), the actuators of the robotic arm 202, the controller 201, a treatment couch, and/or the user interface unit. The electronics module may independently check LINAC positions against a model of surrounding obstructions to ensure that the LINAC 203 does not collide with obstacles during motion of the robotic treatment delivery system 200.

The robotic treatment delivery system 200 is configured to adjust the position and orientation of the LINAC 203 in a 3D workspace or operating envelop in a treatment room under computer control, during therapeutic radiation treatment, using the controller 201. The controller 201 may be coupled to the robotic arm 202, a sensor system, a user interface, an imaging system, a patient positioning system, including a treatment couch. Alternatively, the controller 201 is coupled to more or less components of the radiation treatment system 200.

The robotic treatment delivery system 200 may further include a sensor system for detecting the position of the LINAC 203 and/or a treatment couch; a user interface unit, which allows a user to manually control the motion of the robotic arm 202, and the LINAC 203; and the treatment couch. These components may also be part of a separate system that operates in conjunction with the treatment delivery system 200, such as a patient positioning system 401, as described with respect to FIG. 4A. The controller 201 may be operatively coupled to a sensor system and a user interface unit (described below) of the robotic treatment delivery system 200 in order to calculate the position of the LINAC 203 relative to the treatment room or other predefined treatment coordinate system based on the data received from the sensor system. The controller 201 may also operate to control the motion of the robotic treatment delivery system 200 in a way that a treatment target within the patient's anatomy remains properly aligned with respect to a treatment beam source of the LINAC 203 throughout the treatment procedure. Controller 201 may also be used to operate the positioning of the treatment couch 206.

In one embodiment, the robotic treatment delivery system 200 may be a frameless, image-guided robot-based therapeutic radiation treatment system utilizing a LINAC. Alternatively, the robotic treatment delivery system 200 may be other types of robot based medical systems. In one embodiment, the radiation source is a LINAC, such as LINAC 203. Alternatively, the radiation source may be other types of radiation sources that can be mounted to the distal end of the robotic arm. In one embodiment, the LINAC 203 is an x-ray LINAC. Alternatively, the LINAC 203 may be other types of LINACs known by those of ordinary skill in the art.

In another embodiment, the robotic treatment delivery system 200 includes an x-ray imaging system. The x-ray imaging system generates image data representative of one or more real time or near real time images of the target. The x-ray imaging system may include a pair of diagnostic x-ray sources, and a pair of x-ray image detectors (or cameras), each detector located opposite an associated x-ray source. The treatment couch (or treatment table) supports the patient during treatment, and may be positioned between the two x-ray cameras and their respective diagnostic x-ray sources of the imaging system.

The imaging system generates, in real time or near real time, x-ray images showing the position and orientation of the target in a treatment coordinate frame. The controller 201 may contain treatment planning and delivery software, which may be responsive to pre-treatment scan data CT (and/or MRI data, PET data, ultrasound scan data, and/or fluoroscopy imaging data) and user input, to generate a treatment plan consisting of a succession of desired beam paths, each having an associated dose rate and duration at each of a fixed set of treatment positions or nodes. In response to the controller's directions, the robotic arm moves and orients the LINAC 203, successively and sequentially through each of the nodes, while the LINAC 203 delivers the required dose as directed by the controller. The pre-treatment scan data may include, for example, CT scan data, MRI scan data, PET scan data, ultrasound scan data, and/or fluoroscopy imaging data.

Prior to performing a treatment on a patient therapeutic radiation treatment system 106, the patient's position and orientation within the frame of reference established by imaging system must be adjusted to match the position and orientation that the patient had within the frame of reference of the CT (or MRI or PET or fluoroscopy) scanner that provided the images used for planning the treatment. In one exemplary embodiment, this alignment may be performed to within tenths of a millimeter and tenths of a degree for all of the DOF.

The controller 201 may also communicate with a diagnostic or treatment planning system, receiving pre-treatment scan data representative of one or more pre-treatment scans of a treatment target within the patient. The pre-treatment scans may show the position and orientation of the target with respect to a pre-treatment coordinate system. The controller 201 may also receive from the imaging system (x-ray sources 407 and detectors 408) image data representative of real time or near real time images of the target. The image data may contain information regarding the real time or near real time position and orientation of the target with respect to a treatment coordinate system. The treatment coordinate system and the pre-treatment coordinate system are related by known transformation parameters.

The controller 201 may include an input module for receiving 1) pre-treatment scan data representative of pre-treatment scans of the target, and 2) real time or near real time image data representative of real time or near real time images of the target. The pre-treatment scans show the position and orientation of the target with respect to the pre-treatment coordinate system. The near real-time images, taken by the imaging system under the command of the controller 201, show the position and orientation of the treatment target with respect to the treatment coordinate system. The treatment coordinate system and the pre-treatment coordinate systems are related by known transformation parameters. The controller 201 includes a TLS (target location system) processing unit that computes the position and orientation of the treatment target in the treatment coordinate system, using the pre-treatment scan data, the real time or near real time image data, and the transformation parameters between the pre-treatment coordinate system and the treatment coordinate system. The processing unit of the controller 201 may also compute the position and orientation of the isocenter of the LINAC 203.

The sensor system of the robotic treatment delivery system 200 for detecting the position of the LINAC 203 may be a resolver-based sensor system. Alternatively, other sensor systems known by those skilled in the art may be used, such as an inertial sensor attached to the LINAC 203 for sensing the motions of the LINAC 203, or an infrared triangulation system, or a laser scanning system or an optical tracking system disposed within the treatment room for detecting the position of the LINAC 203 relative to the treatment room or other treatment coordinate system, or an optical encoder.

An exemplary laser scanning system may scan the treatment room approximately 60×/sec to determine the position of the LINAC 203. The laser scanning system may include devices performing a single plane scanning, or two-plane scanning, or multiple-plane scanning. Correspondingly, the controller 201 may be loaded with software adapted for receiving information from the sensor system 104 and calculating the position of the LINAC 203, as well as the treatment couch or other equipment in the treatment room, so that the robotic treatment delivery system 200 including the controller 201 always knows the position of the LINAC 203. The controller 201 may be programmed to automatically or periodically calibrate the LINAC 203 with the treatment couch. In an alternate embodiment, the sensor system includes a magnetic tracking system for tracking the position of the LINAC 203 relative to the treatment coordinate system. The magnetic tracking system preferably includes at least one transducer attached to the LINAC 203.

The controller 201 may be adapted to detect a misalignment of the treatment target with the isocenter of the LINAC 203 caused by patient's movement by comparing the position of the treatment target with the isocenter of the LINAC 203, and generate motion command signals for implementing corrective motions of the robotic treatment delivery system 200 for aligning the treatment target with respect to the radiation treatment source (e.g., LINAC 203).

In another embodiment, the corrective motions of the robotic treatment delivery system 200 may accommodate for various motions, such as respiratory motion; cardiac pumping motion of the patient's heart; sneezing, coughing, or hiccupping; and muscular shifting of one or more anatomical members of the patient.

In another embodiment, the robotic treatment delivery system 200 including the controller 201 may be adapted to detect and accommodate changes in tumor geometry that may be caused by tissue deformation by comparing the real time or near real time image with the pre-treatment image and repositioning the LINAC 203 using the robotic arm 202 and/or the patient using the treatment couch, or adjusting the positions of the LINAC 203 and the treatment couch to correspond to the treatment plan.

The controller 201 includes software for establishing and maintaining a reliable communication interface with the LINAC 203. The software uses the interface specifications developed for the LINAC 203. The controller 201 further includes software for converting the patient position and orientation information from the imaging system to appropriate units of movement in the DOF of motion capability of the LINAC 203. The controller 201 may include software for providing a user interface unit to the treatment delivery system's user control console, to monitor and initiate the motion of the robotic treatment delivery system 200 for positioning the patient. The controller 200 may also include software for detecting, reporting, and handling errors in communication or software control of the LINAC 203.

The controller 201 may include at least one user interface unit for enabling the user to interactively control the motions or corrective motions of the robotic treatment delivery system 200, by implementing one or more user-selectable functions. The user interface unit may be a handheld user interface unit or remote control unit. Alternatively, the user interface unit may be a graphical user interface (GUI) on a display.

The communication links between the controller 201 and other components of the robotic treatment delivery system 200 (e.g., the robotic arm 202, LINAC 203, sensor system, user interface, treatment couch, and imaging system) may be wired links or wireless links, with a bandwidth necessary for maintaining reliable and timely communications.

Figure 2B:
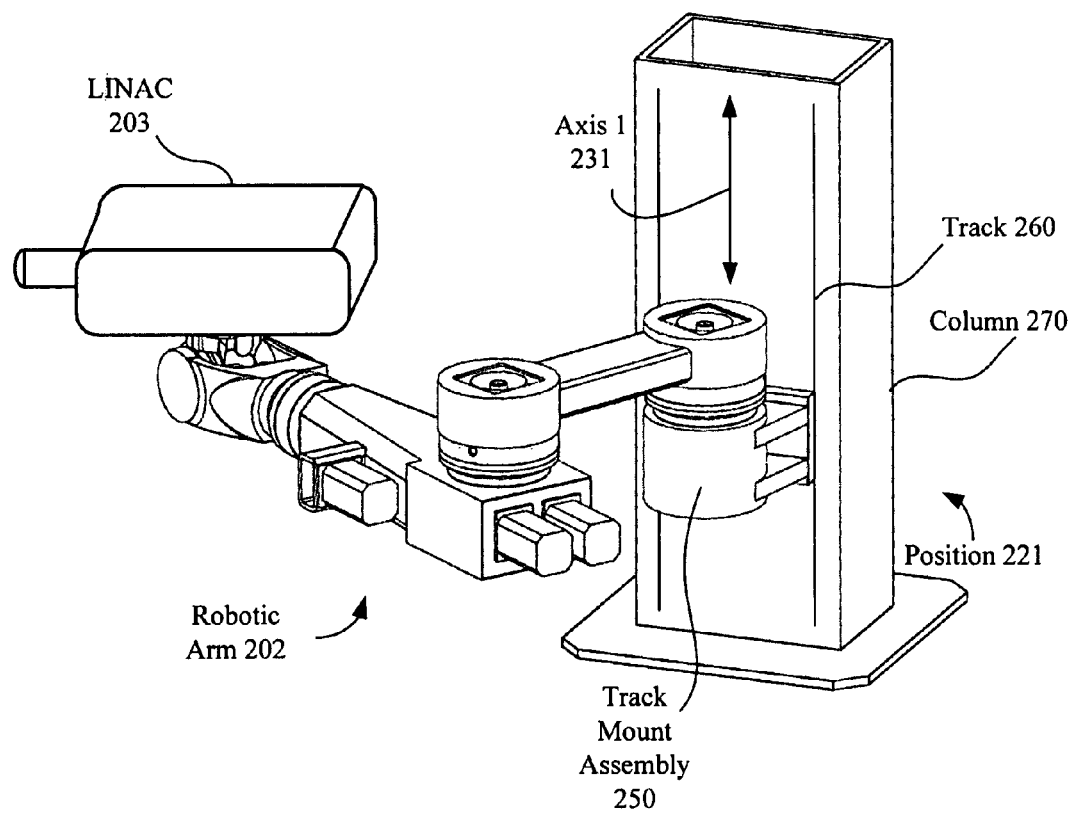
FIG. 2B illustrates one embodiment of a robotic treatment delivery system in a first position along the first axis of the substantially vertical, linear degree of freedom.
Figure 2C:
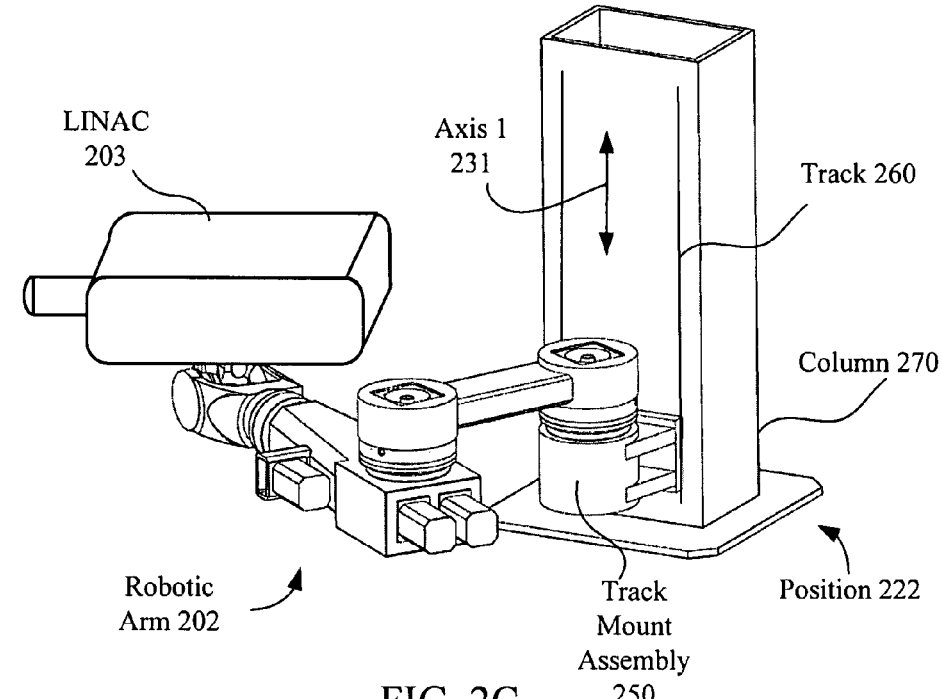
FIG. 2C illustrates another embodiment of the robotic treatment delivery system of FIG. 2B in a second position along the first axis.
Figure 2D:
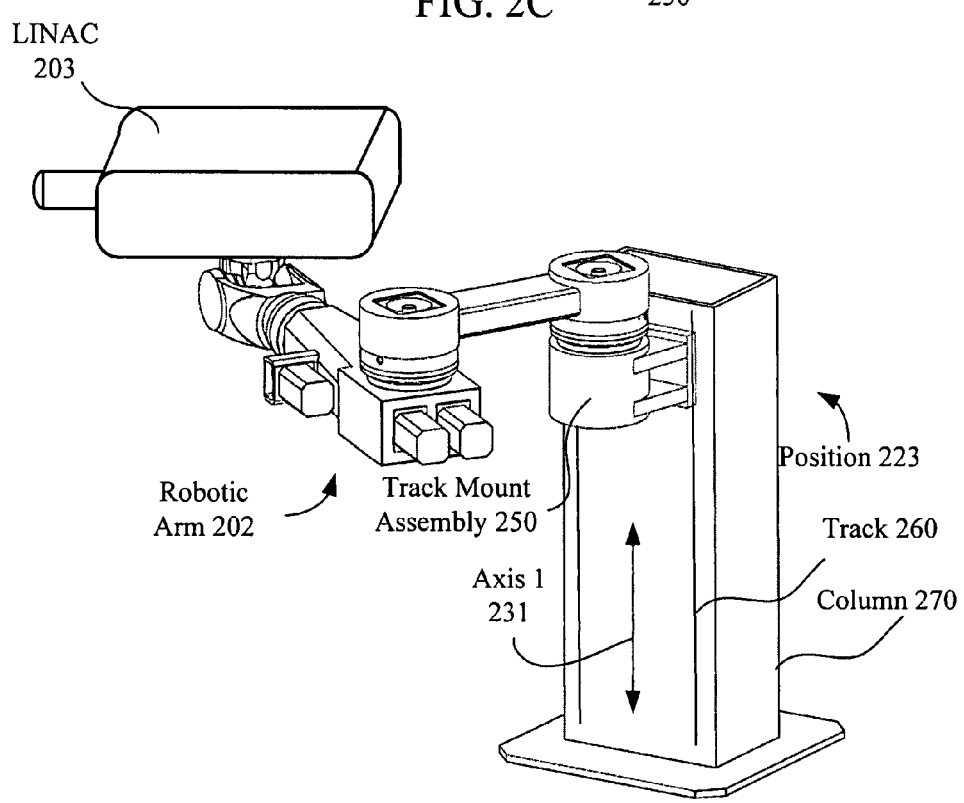
FIG. 2D illustrates another embodiment of the robotic treatment delivery system of FIG. 2B in a third position along the first axis.

FIGS. 2B-2D illustrates one embodiment of the robotic treatment delivery system 200 in three positions 221, 222, and 223 along the first axis 231 of the substantially vertical, linear DOF. The robotic arm 202 has five rotational DOF and one substantially, vertical, linear DOF. In one embodiment, the controller 201 (not illustrated in FIGS. 2B-2D) is configured to move the robotic arm 202 in along the first axis 231 of the first DOF. The first DOF is configured to move the other five rotational DOF of the robotic arm 202. For example, the robotic arm 202 is coupled to the track mount assembly 250, which is coupled to the track 260 of column 270. The controller 201 moves the robotic arm up and down along the axis 231 to different positions. For example, the robotic arm 202 may be positioned in the first position 221, as illustrated in FIG. 2B, in the second position 222, as illustrated in FIG. 2C, and in the third position 223, as illustrated in FIG. 2D. As illustrated in FIGS. 2B-2D, the robotic arm 202 can be configured to move the LINAC 203, as well as the robotic arm 202, along the substantially vertical, linear axis (e.g., axis 231) throughout substantially an entire range of motion of the LINAC 203 without movement of the LINAC 203 along the five rotational DOF.

Also, as illustrated in FIGS. 2B-2D, the substantially, vertical linear DOF is the DOF that is closest to the base end of the robotic arm 202. The base end is where the robotic arm 202 is mounted to the column 270. Alternatively, the base end is where the robotic arm 202 is mounted to the floor, ceiling, wall, or other mounting locations in the treatment room. The LINAC 203 is coupled to the robotic arm 202 at the end-effector end of the robotic arm 202, also referred to as the business end of the robotic arm 202. In another embodiment, the robotic arm 202 has a substantially linear DOF that is horizontal. In another embodiment, the robotic arm 02 has four rotational DOF and one substantially linear DOF, and the first DOF is the substantially linear DOF that is configured to move the other four rotational DOF of the robotic arm. In this embodiment, the controller 201 can move the LINAC along the substantially linear axis (e.g., axis 231 or a horizontal first axis) throughout substantially an entire range of motion of the LINAC 203 without movement of the LINAC 203 along the four rotational DOF. In the embodiment of the first DOF being horizontal, the controller 201 is configured to move the LINAC 203 along a substantially horizontal line in the mutually orthogonal horizontal coordinate axes (e.g., x- and y-axes) that are substantially perpendicular to the vertical axis (e.g., z-axis). In the embodiment of the first DOF being vertical, the controller is configured to move the LINAC 203 along a substantially vertical line in the vertical axis (e.g., z-axis) that is substantially perpendicular to the mutually orthogonal horizontal coordinate axes (e.g., x- and y-axes).

In another embodiment, the robotic arm includes six rotational DOF and one substantially linear DOF that is configured to move the other six rotational DOF of the robotic arm. In this embodiment, the controller 201 can move the LINAC along the substantially linear axis (e.g., axis 231 or a horizontal first axis) throughout substantially an entire range of motion of the LINAC 203 without movement of the LINAC 203 along the six rotational DOF. In the embodiment of the first DOF being horizontal, the controller 201 is configured to move the LINAC 203 along a substantially horizontal line in the mutually orthogonal horizontal coordinate axes (e.g., x- and y-axes) that are substantially perpendicular to the vertical axis (e.g., z-axis). In the embodiment of the first DOF being vertical, the controller is configured to move the LINAC 203 along a substantially vertical line in the vertical axis (e.g., z-axis) that is substantially perpendicular to the mutually orthogonal horizontal coordinate axes (e.g., x- and y-axes).

Figure 2E:
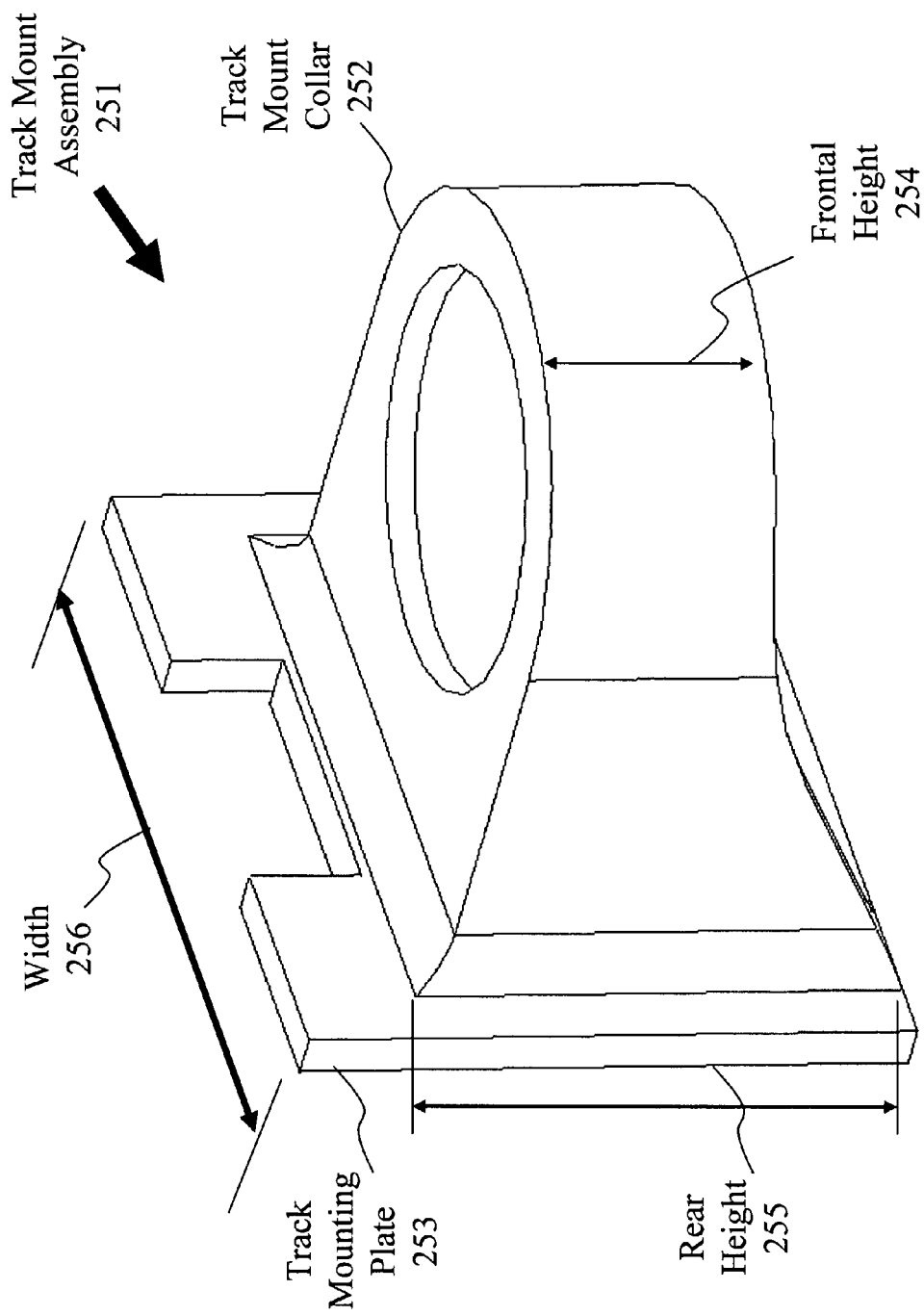
FIG. 2E illustrates one embodiment of a track mount assembly.

FIG. 2E illustrates one embodiment of a track mount assembly 251. Track mount assembly 251 is coupled to the track 260 and shoulder assembly 240 of FIG. 2A. It should be noted that description herein with respect to the structure and operations of the track mount assembly 250 of robotic arm 202 apply to track mount assembly 251. The track mount assembly 251 includes a track mount collar 252 and a track mount plate 253. In one embodiment, the track mount collar 252 and the track mount plate 253 may be separate components. Alternatively, the track mount collar 252 and a track mount plate 253 may be one integral piece. Track mount collar 252 includes a frontal height 254, and a rear height 255, the rear height 255 being closer to the track than the frontal height 254. In one embodiment, the rear height of the track mount collar 252 may be at least eleven inches (11"). In another embodiment, the track mount collar 252 may taper down in height from the end closest to the track mount plate 253 being greater in height than the end farthest away from the track mount plate 253. In such embodiment, the frontal height 254 at the end farthest away from the track mount plate 253 may be at least five inches (5"), while the rear height 255 at the end closest to the track mount plate 253 may be at least eleven inches (11"). Alternatively, the track mount collar 252 may have other dimensions.

Figure 2F:
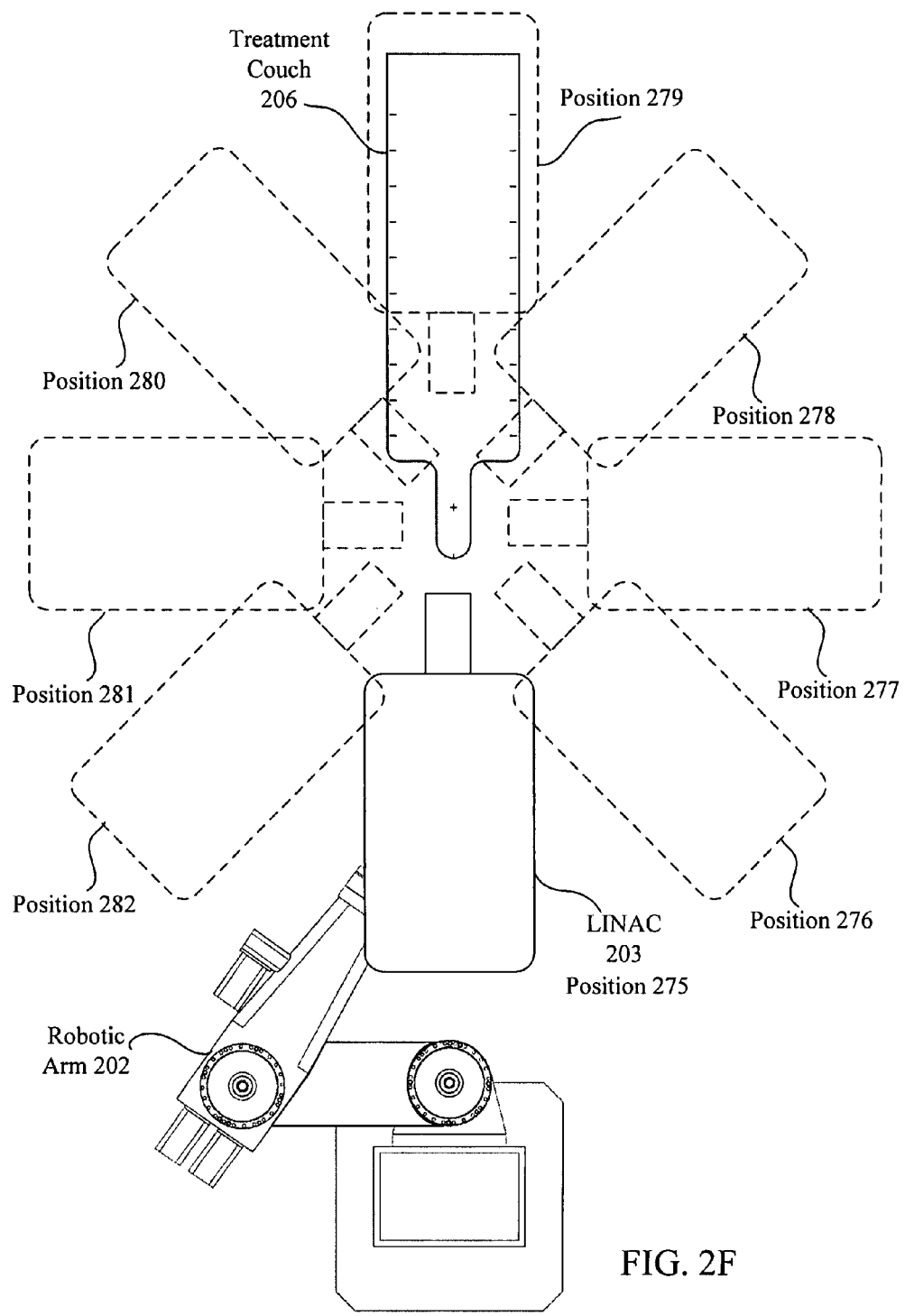
FIG. 2F illustrates a top side view of one embodiment of a LINAC, which is coupled to a robotic arm, in various positions with respect to a treatment couch.

FIG. 2F illustrates a top side view of one embodiment of a LINAC 203, which is coupled to a robotic arm 202, in various positions with respect to a treatment couch 206. The robotic arm 202 includes five DOF, including for rotational DOF and one substantially vertical, linear DOF (e.g., axis 231). The controller 201 is configured to move the robotic arm 202 into various positions 275-282 in the workspace of the LINAC 203 with respect to the treatment couch 206. Positions 275-282 are exemplary positions of the LINAC 203 with respect to the head end of the treatment couch 206 along a horizontal plane. Alternatively other positions and orientations of the LINAC 203 within the workspace are possible, such as the positions of the LINAC 203 described with respect to FIGS. 2G-2J.

Figure 2H:
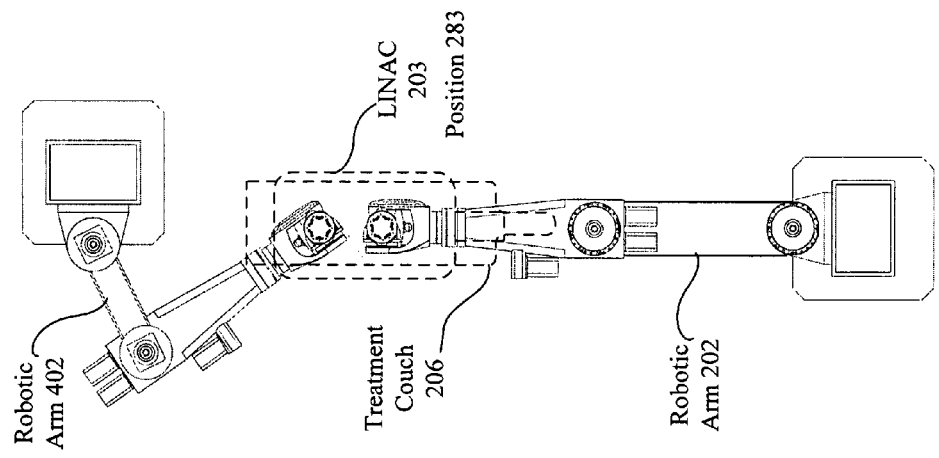
FIG. 2H illustrates one embodiment of the LINAC of FIG. 2F, which is coupled to the first robotic arm, in a second position with respect to the treatment couch coupled to a second robotic arm.
Figure 2G:
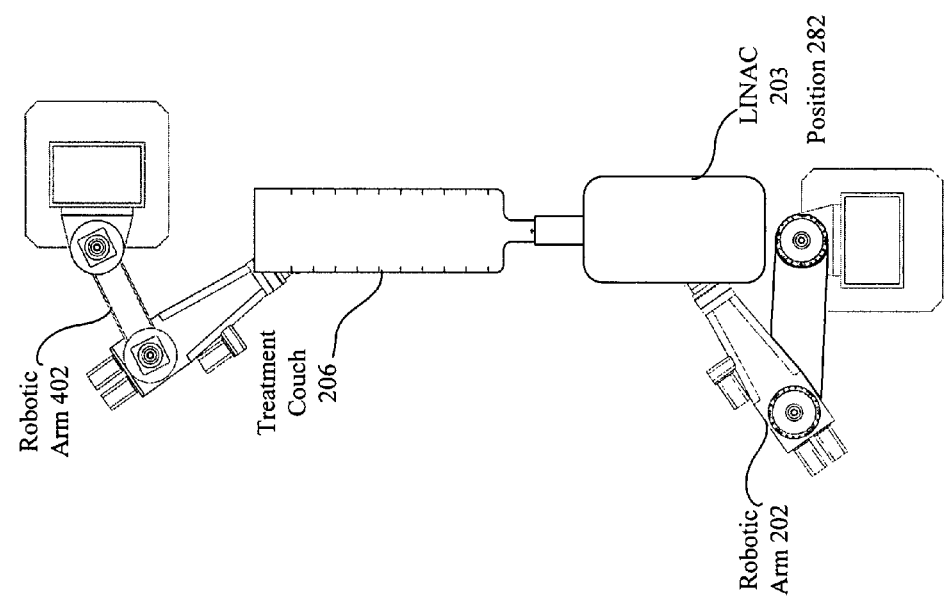
FIG. 2G illustrates one embodiment of the LINAC of FIG. 2F, which is coupled to a first robotic arm, in a first position with respect to a treatment couch coupled to a second robotic arm.

FIGS. 2G and 2H illustrate top side views of one embodiment of the LINAC 203 of FIG. 2F, which is coupled to a first robotic arm 202, in a first position and a second with respect to a treatment couch 206 coupled to a second robotic arm 402. In the embodiment of FIG. 2G, the LINAC 203 is positioned at the first position 282 using the controller 201. The LINAC 203 at the first position 282 is configured to direct one or more radiation beams towards the head end of the treatment couch 206, such as to a target within the head of a patient that is lying on the treatment couch 206. In the embodiment of FIG. 2H, in the LINAC 203 is positioned at the second position 283 using the controller 201. The LINAC 203 at the second position 203 is configured to direct one or more radiation beams towards the head and of the treatment couch 206, such as to the target within the head of the patient that is lying on the treatment couch 206. The LINAC 203 at the second position 283 may direct radiation to the target within the patient from a different direction than the first position 283 of the LINAC 203. Alternatively, the LINAC 203 at the second position 283 may direct radiation from both a different direction and a different angle by moving both the position and the orientation of the LINAC 203 with respect to the target. In another embodiment, the LINAC 203 at the position 283 is configured to direct radiation to a target in a posterior treatment. During posterior treatments, with the patient lying in supine position on the treatment couch, the LINAC may be positioned to be pointed upwards at the patient and deliver the treatment beam from the posterior direction.

The robotic arm 202 may be configured to position and orient the LINAC 203 in positions that were previously blocked using conventional robotic arms. For example, the robotic arm 202 can position and orient the LINAC 203 above the patient using the substantial vertical, linear DOF (e.g., track 260) and the second and third DOF (e.g., shoulder and elbow assemblies 240 and 230) to provide the vertical reach, while the wrist axis 220 provides the orientation of the LINAC 203 with respect to a target in a posterior treatment (e.g., rotate the LINAC 203 about the pitch-axis (axis 5 of FIG. 2A) using the tool-yaw joint of the wrist assembly 220). Alternatively, the LINAC 203 may be positioned and oriented with respect to the target in posterior treatments using other motions of the robotic arm 202. Alternatively, the LINAC 203 at the position 283 is configured to direct radiation to a target in other types of treatments.

In the embodiments of FIGS. 2G and 2H, the treatment couch 206 is coupled to the robotic arm 402, which includes five DOF, including for rotational DOF and one substantially vertical, linear DOF. The robotic arm 402 is configured to move the treatment couch 206 with respect to the LINAC 203. The robotic arm 402 may be coupled to controller 201. Alternatively the robotic arm 402 may be coupled to a separate controller. The controller 201 may be used to coordinate the movements of both the LINAC 203 and the treatment couch 206 relative to one another. This may allow the LINAC 203 to be positioned and oriented with respect to the treatment couch in additional positions that may have been previously obstructed for conventional systems. In another embodiment, the LINAC 203 can be positioned with respect to a treatment couch 206 that is not coupled to a robotic arm, such as a treatment couch mounted to a stand, to the floor, to an Axum® treatment couch, developed by Accuray Inc., of Sunnyvale, Calif., or to other patient positioning systems.

Figure 2J:
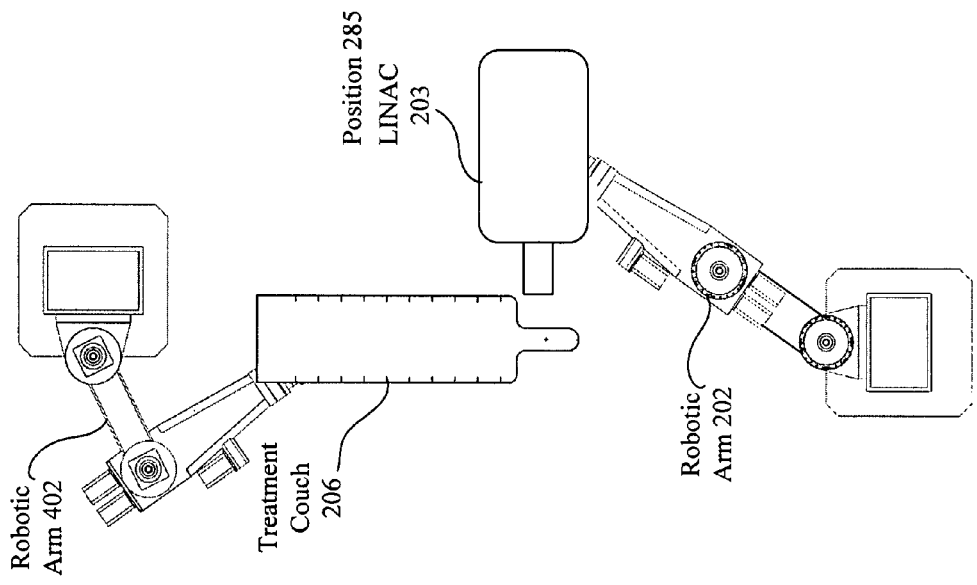
FIG. 2J illustrates one embodiment of the LINAC of FIG. 2F, which is coupled to the first robotic arm, in a fourth position with respect to the treatment couch that is symmetrical with the third position.
Figure 2I:
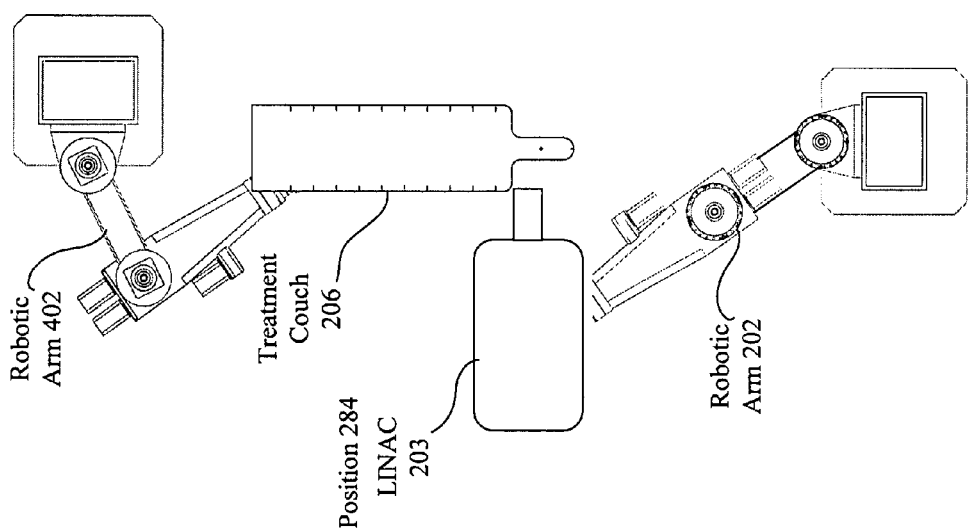
FIG. 2I illustrates one embodiment of the LINAC of FIG. 2F, which is coupled to the first robotic arm, in a third position with respect to the treatment couch coupled to the second robotic arm.

Using the robotic arm 202 the LINAC 203 may be positioned in symmetrical positions with respect to the treatment couch 206 such as described in FIGS. 2I and 2J. FIGS. 2I and 2J illustrate top side views of one embodiment of the LINAC 203 of FIG. 2F, which is coupled to the first robotic arm 202, in a third position 284 and a fourth position 285 with respect to the treatment couch 206. The third position 284 and the fourth position 285 are symmetrical positions with respect to the treatment couch 206. The capability of positioning the LINAC 203 with respect to the treatment couch 206 in the symmetrical locations may lead to simplified paths for path planning and contact avoidance planning, calculated before treatment delivery, such as calculated by a treatment planning system during treatment planning. The capability of positioning the LINAC 203 with respect to the treatment couch 206 in symmetrical locations may increase the workspace within which the LINAC 203 may be positioned to direct radiation to a target. The access to direct radiation to targets within various locations of the patient may be increased because the number of nodes in the workspace is increased. For example, the nodes on one side of the treatment couch 206 may also be mirrored on the other side of the treatment couch 206, as illustrated in FIGS. 2I and 2J.

In one embodiment, the robotic arm 202 and the robotic arm 402 are identical robotic arms. In one embodiment, the robotic arms 202 and 402 each include four rotational DOF and one substantially linear DOF. In another embodiment, the robotic arms 202 and 402 each include five rotational DOF and one substantially linear DOF. Alternatively, the robotic arms 202 and 402 each include six rotational DOF and one substantially linear DOF. Alternatively, the robotic arms 202 and 402 may include dissimilar number and types of DOF. In another embodiment, the robotic arm 202 and the robotic arm 402 are dissimilar types of robotic arms. Alternatively, only the robotic arm 202 is used to move the LINAC 203 with respect to the treatment couch 206.

In another embodiment, the robotic arm 202 coupled to the LINAC 203 can be used in a smaller room size, as compared to conventional robotic arms coupled to LINACs. The smaller room size, such as the footprint of the robotic arm, can be realized due to the different mounting of the LINAC to the robotic arm.

Figure 3:
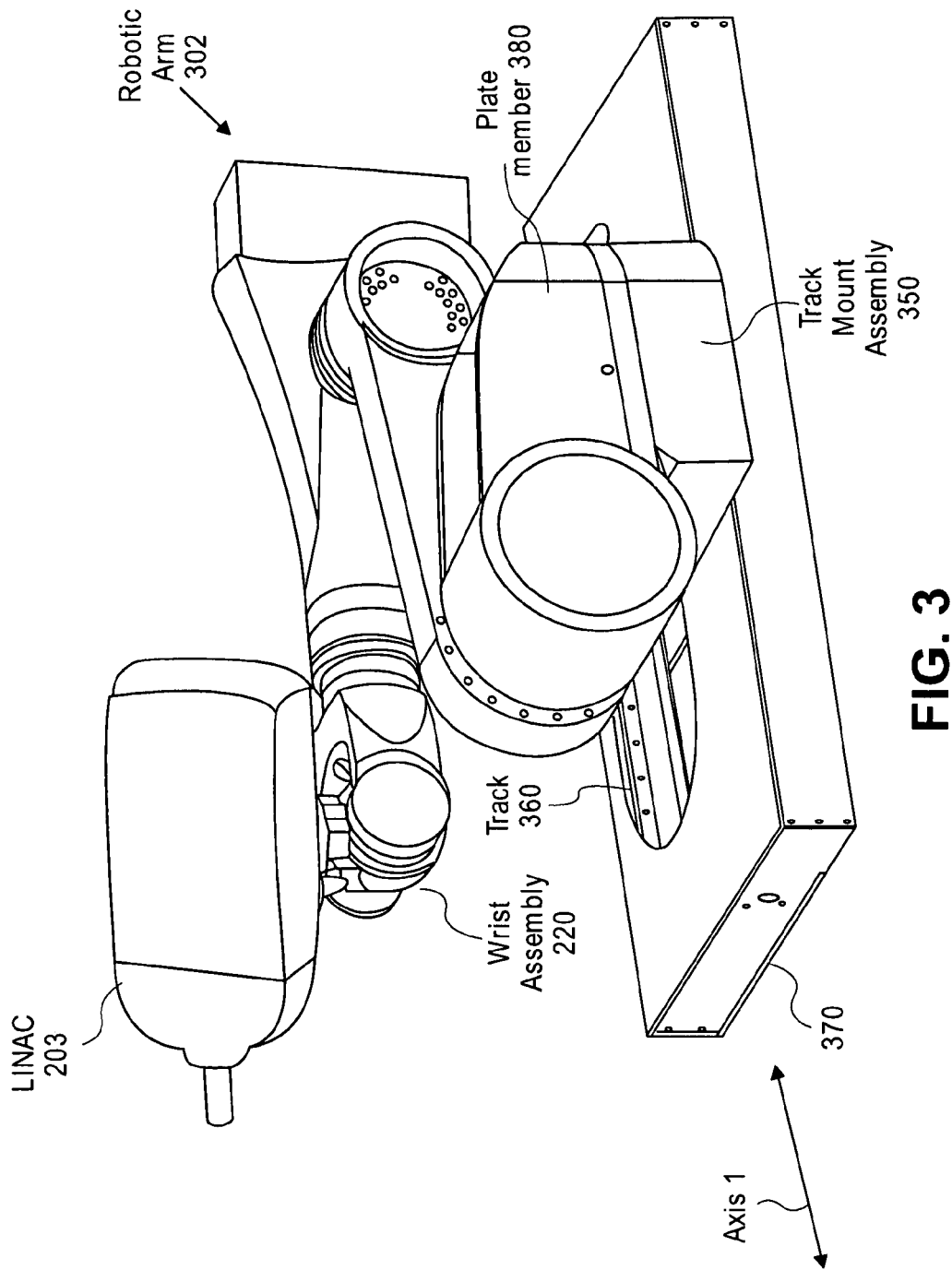
FIG. 3 illustrates one embodiment of a robotic treatment delivery system having a robotic arm having six rotational degrees of freedom and one substantially horizontal, linear degree of freedom.

FIG. 3 illustrates one embodiment of a robotic treatment delivery system 300 including a robotic arm 302 having six rotational DOF and one substantially horizontal, linear DOF. As shown in FIG. 3, the robotic treatment delivery system 300 includes a robotic arm 302 having a wrist assembly 220, an elbow assembly 230, a shoulder assembly 240, a plate member 380, a track mount assembly 350, and a track 360 encased in a track encasing 370, and a LINAC 203. As described above, the LINAC 203 may be rotatably attached to the wrist assembly 220, which includes a tool-yaw joint, a tool-pitch joint, and a tool-roll joint. The tool-yaw joint of wrist assembly 220 may be coupled to a mounting plate, which is attached to the bottom of the LINAC 203, or directly to the housing of the LINAC 203. The tool-yaw joint of wrist assembly 220 facilitates rotational movement of the LINAC 203 in a yaw-rotation along a yaw axis, axis 7 of FIG. 3. The tool-pitch joint may be coupled to the tool-yaw joint and facilitates rotational movement of the LINAC 203 in a pitch-rotation along a pitch axis, axis 6 of FIG. 3. The tool-roll joints may be coupled to the tool-pitch joint and facilitates rotational movement of the LINAC 203 in a roll-rotation along a roll axis, axis 5 of FIG. 3.

The elbow assembly 230 may be coupled to the tool-roll joint of wrist assembly 220. The elbow assembly 230 includes three drive shafts and three motors. The first drive shaft may be coupled to the tool-yaw joint and the first motor. The first motor and drive shaft drive rotational movement of LINAC 203 along the yaw axis, axis 7 of FIG. 3. The second drive shaft may be coupled to the tool-pitch joint and the second motor. The second motor and drive shaft drive rotational movement of the LINAC 203 along the pitch axis, axis 6 of FIG. 3. The third drive shaft may be coupled to the tool-roll joint and the third motor. The third motor and drive shaft drive rotational movement of the LINAC 203 along the roll axis, axis 5 of FIG. 3. In one exemplary embodiment, the elbow assembly 230 is ten inches (10") in diameter at the distal end that connects to the tool-roll joint of the wrist assembly 220. Alternatively, the elbow assembly 230 may have a diameter that is approximately three to twenty inches (3"-20"). Alternatively, the elbow assembly 230 may have another shape than circular, for example, rectangular, oval, or other known shapes, and the elbow assembly 230 may have a minimum measurement of its cross section between three (3") to twenty (20") inches. In one embodiment, the ten inch diameter of the elbow assembly coupled to the LINAC 203 enables support of a load up to five hundred pounds within a deflection error of approximately zero to five millimeters (0 to 5 mm) of the LINAC 203. Alternatively, other dimensions may be used.

The shoulder assembly 240 may be coupled to the elbow assembly 230 by an elbow joint and to the track mount assembly 350 by a shoulder joint. The elbow joint includes an elbow gearbox, which may be configured to drive rotational movement of the elbow assembly 230 of the robotic arm in a rotational axis, axis 4 of FIG. 3. The shoulder joint includes a shoulder gearbox, which may be configured to drive rotational movement of the shoulder assembly 240 of the robotic arm in a rotational axis, axis 3 of FIG. 3. The elbow and shoulder gearboxes of the shoulder and elbow assemblies 230 and 240 facilitate translational movement of the LINAC 203 in a two-dimensional horizontal plane, for example, in the (x-, y-) plane parallel with the floor. In one embodiment, the elbow and shoulder gearboxes have approximately a two hundred to one gear reduction ratio (200:1). The 200:1 gear reduction ratio of the elbow and shoulder gearboxes may enable support of a load up to five hundred pounds within a deflection error on the LINAC 203, being approximately in a range of zero to sixty millimeters (0 to 60 mm). In one exemplary embodiment, the deflection error 261 is approximately zero to five millimeters (0 to 5 mm). Alternatively, the gear reduction ratios may range from approximately ten to one gear reduction ratio (10:1) to approximately six hundred to one gear reduction ratio (600:1). Alternatively, other gear reduction ratios and dimensions may be used, as described above.

The plate member 380 may be coupled to the shoulder joint of the shoulder assembly 240 and rotatably mounted to the track mount assembly 350. The plate member includes a gearbox, which may be configured to drive rotational movement of the plate member 380 of the robotic arm in a rotational axis, axis 2 of FIG. 3. The gearbox of the plate member facilitates translational movement of the LINAC 203 in a horizontal plane substantially parallel to the floor. In one embodiment, the gearbox of the plate member 380 has a gear reduction ratio. The gear reduction ratio of the gearbox of the plate member 380 may range from approximately two hundred and fifty to one to approximately three hundred to one (250:1 to 300:1). In one exemplary embodiment, the gear reduction ratio of the plate member gearbox is approximately 300:1. Alternatively, other gear reduction ratios may be used as described above.

In one embodiment, the track mount assembly 350 has similar dimensions as set forth in the discussion above with respect to FIG. 2E. Alternatively, other dimensions may be used.

In one embodiment, the wrist, elbow, and shoulder assemblies 220, 230, and 240 and the plate member 380 of the robotic arm 302 may include components manufactured by KUKA Roboter GmbH of Germany. Alternatively, the wrist, elbow, and shoulder assemblies 220, 230, and 240 and the plate member 380 of the robotic arm 302 may include other types of components.

The track mount assembly 350 may be coupled to a track 360 and to the plate member 380. The track mount assembly 350 and track 360 facilitate translational movement of the LINAC 203 in a substantially horizontal, linear axis, axis 1 of FIG. 3. The substantially horizontal, linear axis (x-, y-) is substantially perpendicular to the two dimensional vertical plane (z-). In this embodiment, track 360 is mounted to the floor and is encased in a track encasing 370. In another embodiment, the track 360 is coupled to the floor. In another embodiment, the track 360 may be vertically oriented, for example, vertically mounted to a vertical side of column 270. The column 270 may be secured or mounted to the floor of the treatment room during therapeutic radiation treatment or below the floor in a pit. In another embodiment, column 270 may be secured or mounted to the ceiling of the treatment room during therapeutic radiation treatment. Alternatively, the track 360 may be vertically mounted to other structures known to those skilled in the art, such as a wall, pedestal, block, or base structure.

The abovementioned arrangement of the wrist assembly 220, elbow assembly 230, shoulder assembly 240, plate member 380, track mount assembly 350, and track 360 facilitate the positioning of the LINAC 203 using six rotational DOF and one translational substantially horizontal, linear DOF. The six rotational and one substantially horizontal, linear DOF of the robotic arm 302 of the robotic treatment delivery system 200 may position the LINAC 203 in substantially any place in a desired treatment area, such as a workspace, within the mechanical range of motion of the robotic arm 302. The robotic arm 302 may position the LINAC 203 to have a tool center position (TCP) in multiple locations within the workspace or treatment area. In one embodiment, the six DOF includes three rotational axes for translational movements along mutually orthogonal coordinate axes (x-, y-, and z-axes); and three rotational axes for roll-, pitch-, and yaw-rotational movements about x-, y-, and z-axes, respectively. The one substantially horizontal, linear DOF includes a substantially linear axis for translational movement along a substantially horizontal line in a coordinate axis (x-, and y-axes) substantially perpendicular to the vertical coordinate axes (z-axis).

In one embodiment, the robotic arm 302 includes one or more motion actuators for moving the LINAC 203, in accordance with directions from the controller 201. An interface module may allow the LINAC 203 to interface with the sensor system, the actuators of the robotic arm 302, the controller 201, a treatment couch, and/or the user interface unit. The electronics module may independently check LINAC positions against a model of surrounding obstructions to ensure that the LINAC 203 does not collide with obstacles during motion of the robotic treatment delivery system 300.

In one embodiment, the robotic arm 202 or 302 is configured to move the LINAC 203 along a single axis without moving the LINAC 203 along the other axes throughout an entire range of motion of the LINAC 203. For example, the first DOF is configured to move the LINAC 203 along a substantially linear axis through substantially an entire range of motion of the robotic arm without movement of the LINAC 203 along the four, five, or six rotational DOF. The first DOF is the DOF that is closest to the base end of the robotic arm.

As described above, the LINAC 203 is capable of motion in five DOF (e.g., four rotational DOF and one substantially linear DOF), namely one translational DOF (x- and y-axes), three rotational DOF (yaw-, pitch-, and roll-axes), and one substantially linear DOF (either substantially vertical or horizontal). Alternatively, the LINAC 203 is capable of motion in six DOF, namely two translational DOF (x- and y-axes) (axes 2 and 3, respectively, of FIG. 2A), three rotational DOF (yaw-, pitch-, and roll-axes) (axes 6, 5, and 4 of FIG. 2A), and one substantially vertical, linear DOF (substantially vertical, linear axis) (axis 1 of FIG. 2A). Alternatively, the LINAC 203 may be capable of motion in seven DOF, namely three translational DOF (x-, y-, and z-axes) (axes 4, 3 and 2, respectively, of FIG. 3) plus three rotational DOF (roll-, pitch- and yaw-rotations) (axes 7, 6, and 5, respectively, of FIG. 3), and one substantially vertical, linear DOF (substantially vertical, linear axis) (axis 1 of FIG. 3). The motion command signals, generated by the controller 201, may control corrective motions of the robotic treatment delivery system 200 in the various DOF. In one embodiment, the position and orientation of the LINAC 203 with respect to the treatment couch 206 may be known, so that coordinated movements may be effected. In one exemplary embodiment, both the LINAC 203 and the treatment couch 206 can be referenced to a common (or "room") coordinate system.

Figure 4A:
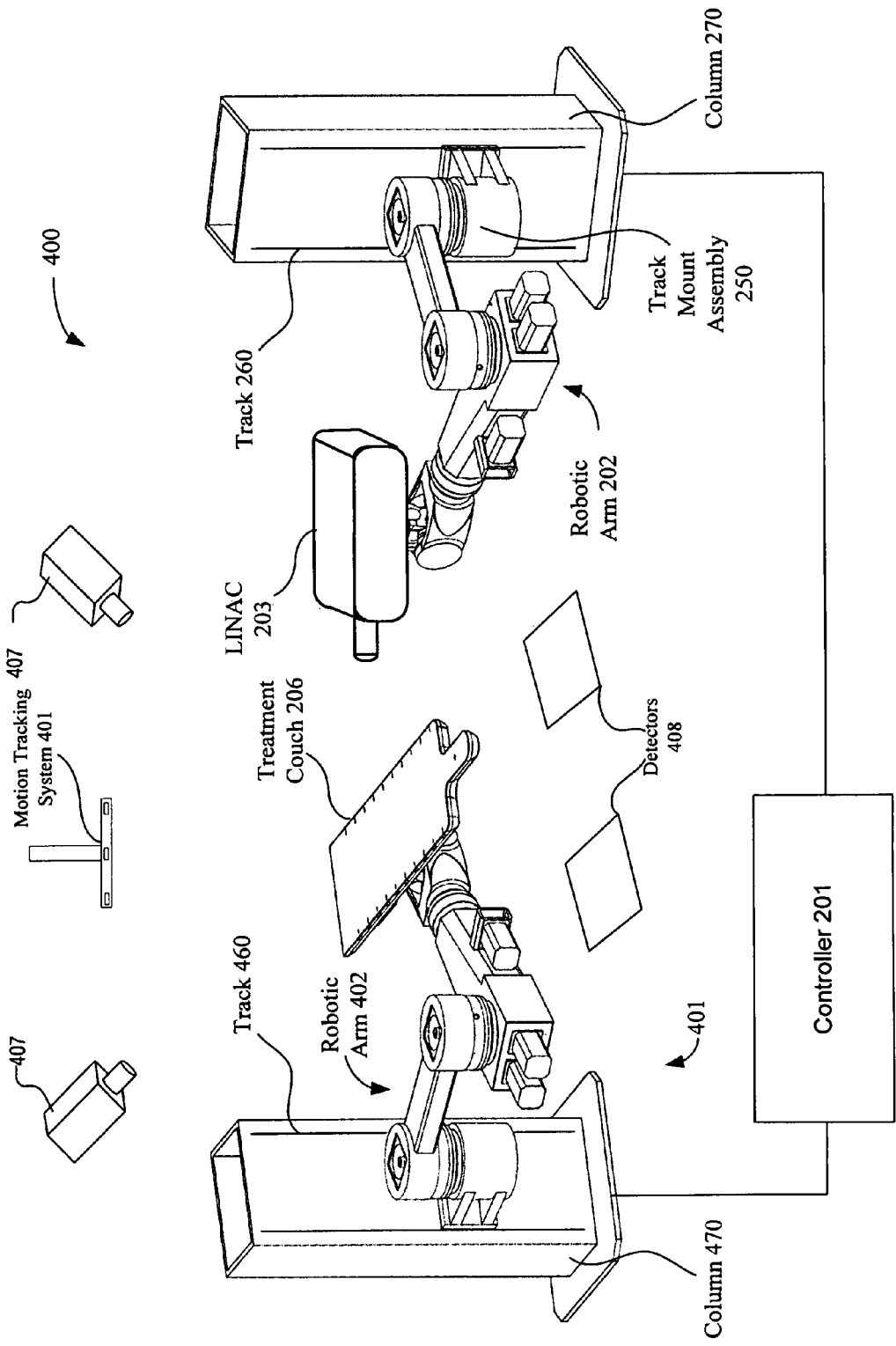
FIG. 4A illustrates one embodiment of a system having the robotic treatment delivery system of FIG. 2A and a robot-based patient positioning system.

FIG. 4A illustrates one embodiment of a system 400 having the robotic treatment delivery system 200 of FIG. 2A and a robot-based patient positioning system 401. The robotic treatment delivery system 200 of FIG. 4A includes similar components as described with respect to FIGS. 2A-2I. The robot-based patient positioning system 401 includes a robotic arm 402 and a treatment couch 206 coupled to a distal end of the robotic arm 402. In one embodiment, the treatment couch 206 may be made of a radiolucent material so that the patient could be imaged through the treatment couch 206. An exemplary imaging system that can be used with the system 400 includes two x-ray imaging sources 407, power supplies associated with each x-ray imaging source, one or two imaging detectors 408, and controller 201. The x-ray imaging sources 407 may be mounted angularly apart, for example, about 90 degrees apart, and aimed through the treatment target (e.g., tumor within the patient) toward the detector(s) 408. Alternatively, a single large detector may be used that would be illuminated by each x-ray source. In the single detector imaging system, the two x-ray sources 407 may be positioned apart at an angle less than 90 degrees to keep both images on the single detector surface.

The detector(s) 408 may be placed below the treatment target, e.g., on the floor, on the treatment couch 206, or underneath the LINAC 203, and the x-ray imaging sources 407 may be positioned above the treatment target (e.g. the ceiling of the treatment room), to minimize magnification of the images and therefore the required size of the detector(s) 408. In an alternative embodiment, the positions of the x-ray imaging sources 407 and the detector(s) 408 may be reversed, e.g. the x-ray imaging sources 407 below the treatment target and the detector(s) 408 above the treatment target. In another embodiment, the detector(s) 408 are arranged in a manner such that they move into position for imaging and the moved out of the way during positioning of the LINAC 203 or the treatment couch 206 or during delivery of the radiation beam from the LINAC 203.

The detector(s) 408 may generate the image information of the patient and send it to the controller 201. The controller 201 performs all the imaging calculations to determine the patient's position with respect to the desired treatment position and generate corrections for the various DOF. The corrections could be automatically applied to the robotic treatment delivery system 200 to automatically align the LINAC 203, and/or sent to the controller 201 to automatically adjust the patient's position using the treatment couch 206 and robotic arm 402 relative to the LINAC 203, and/or sent to the user interface unit for a user to manually adjust the patient's position relative to the LINAC 206, using one or both of the robotic arms 202 and 402.

In one embodiment, the robotic arm 202 and the robotic arm 402 are identical robotic arms. In one embodiment, the robotic arms 202 and 402 each include four rotational DOF and one substantially linear DOF. In another embodiment, the robotic arms 202 and 402 each include five rotational DOF and one substantially linear DOF. Alternatively, the robotic arms 202 and 402 each include six rotational DOF and one substantially linear DOF. Alternatively, the robotic arms 202 and 402 may include dissimilar number and types of DOF. In another embodiment, the robotic arm 202 and the robotic arm 402 are dissimilar types of robotic arms.

As previously mentioned, the robotic treatment delivery system 200 including the controller 201 may know the position of the LINAC 203 through the sensor system and the position of the treatment target through the real time or near real time image data, and also knows the position of the treatment couch 206 and may generate motion command signals for implementing corrective motions of either the robot-based patient positioning system 401 or the robotic treatment delivery system 200 for aligning the treatment target with respect to the radiation source of the LINAC 203. In one embodiment using a robot-based patient positioning system 401, the corrective motions of the robotic treatment delivery system 200 may be dynamically coordinated with the motions of the treatment couch 206 and robotic arm 402 using the controller 201, in a way as to maximize the workspace available to the system 400. By dynamically coordinating the motions of the treatment couch 206 and the LINAC 203 using the controller 201, the available number of treatment targets increases due to the increased number of orientations and positions of the LINAC 203 and the treatment couch 206, which are free of obstructions, for example, by detectors 408 and/or x-ray imaging sources 407, robotic arms, or other equipment within the treatment room. In this embodiment, the robot-implemented movements of the LINAC 203 are complemented by the corrective motions of the treatment couch 206, so that the relative motion between the LINAC 203 and the treatment couch 206 ensures the delivery of the desired radiation pattern throughout the target region.

The robotic arm 202 may position the LINAC 203 to have a tool center position (TCP) or treatment target in multiple locations within the workspace or treatment area. The robotic arm 402 of the robot-based patient positioning system 401 may also position the isocenter or machine center of the patient positioning system 401 in multiple locations within the workspace or treatment area. The workspace or treatment area, however, may be limited by positioning restrictions, for example, obstructions caused by a possible collisions between either the LINAC 203, the treatment couch 206, or their corresponding robotic arms with components of the system 400, such as the LINAC 203, treatment couch 206, imaging sources 407, detectors 408, and/or robotic arms 202 and 402 or obstructions of the radiation beam of the LINAC 203 with any of these above mentioned components. For example, the x-ray imaging sources 407 may prevent the LINAC 203 from being positioned where the x-ray imaging sources 407 are mounted because positioning it there would result in a possible collision (e.g., collision obstructions). Similarly, the LINAC 203 may not be positioned under the treatment couch 206 due to the placement of the detectors 408 (e.g., collision obstructions). Another example of a positioning restriction is obstructions of the radiation beam from the LINAC 203 due to other components, for example, the detectors 408 and/or x-ray imaging sources 407 (e.g., beam obstructions).

In one embodiment, the controller 201 may be configured to dynamically move independently, or in combination the LINAC 203 along at least four rotational DOF and one substantially linear DOF using the robotic arm 202, and the treatment couch 206 along at least four rotational DOF and one substantially linear DOF using the robotic arm 402 to dynamically coordinate orientation and position of the LINAC 203 and the treatment couch 206. The dynamic coordination of movement between the treatment couch 206 and the LINAC 203 may increase a number of treatment targets within a mechanical range of motion of the robotic arm.

The controller 201 may be configured to position the LINAC 203 and the treatment couch 206 to create a treatment target in a previously obstructed location caused by a positioning restriction within a mechanical range of motion of the robotic arm 202 of the LINAC 203. Alternatively, the controller 201 may be configured to position the LINAC 203 and the treatment couch 206 to create a treatment target in a previously obstructed location caused by a positioning restriction within a mechanical range of motion of the robotic arm 402 of the treatment couch 206. In one embodiment, the previously obstructed location may be caused by an obstruction of a possible collision, for example, between either the LINAC 203, treatment couch 206, their corresponding robotic arms with the robotic arm 202, robotic arm 402, the LINAC 203, the LINAC 203, x-ray imaging sources 407, detectors 408, and/or other components of the system 400. Alternatively, the previously obstructed location may be caused by an obstruction of the radiation beam of the LINAC with the robotic arm 202, robotic arm 402, the LINAC 203, the LINAC 203, x-ray imaging sources 407, detectors 408, and/or other components of the system 400.

In one embodiment, an anti-collision model may be embedded in the controller 201 to ensure that the patient is not positioned in an orientation and/or position that might cause a possible collision between the treatment couch 206 including the patient's body and other moving parts of the system 400.

Figure 4B:
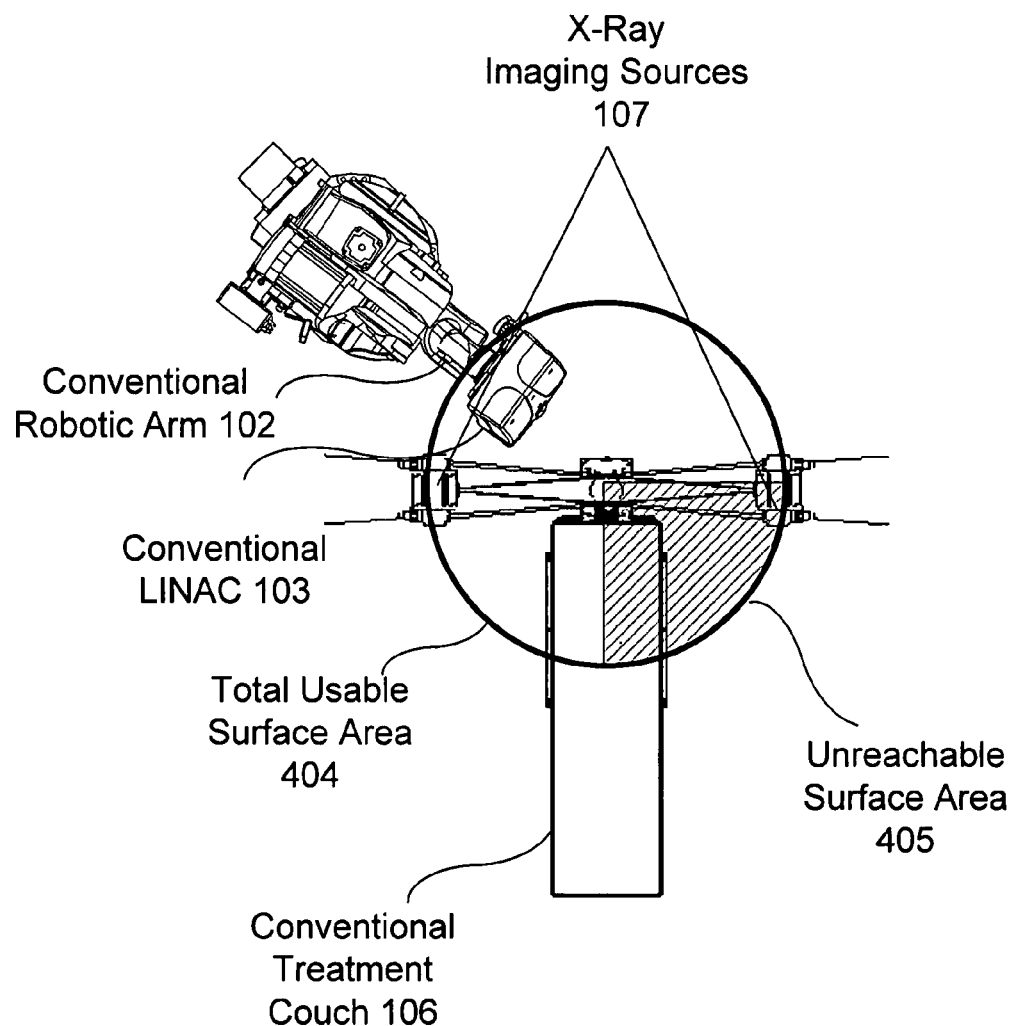
FIG. 4B illustrates a top-down view of a total usable surface area of a conventional treatment couch and a conventional LINAC disposed on a first side of the conventional treatment couch.

FIG. 4B illustrates a top-down view of a total usable surface area of a conventional treatment couch 106 and a conventional LINAC 103 disposed on a first side of the conventional treatment couch 106. In this embodiment, the robotic arm 102 of the conventional LINAC 103 is disposed on floor on one side (e.g., the first side) of the treatment couch 106. The LINAC 103 may be positioned using the robotic arm 102 of in a 3D workspace within the mechanical range of motion of the robotic arm 102. The LINAC 103 may be positioned to be a certain distance from the treatment target within the patient on the conventional treatment couch 106. The certain distance between the LINAC 103 and the treatment target of the patient is the source axis distance (SAD). Since the robot-based LINAC 103 may be positioned and oriented within the 3-D workspace using the robotic arm 102, the LINAC 103 has a total usable surface area 404, which may be dependant upon the SAD. In one embodiment, if the SAD is a fixed number, the total usable surface area 404 would have approximate spherical shape. Alternatively, other usable surface areas may be used of different shapes that have been obtained by varying the SAD. The total usable surface area 404 may represent the positions or nodes in which the LINAC 103 (e.g., x-ray LINAC) may be positioned to emit radiation to the treatment target within the patient. The total usable surface area 404 may be limited by positioning restrictions as described above.

In one embodiment, the positioning restriction may be caused by a treatment table or couch. In one exemplary embodiment, the position restriction may cause an unreachable surface area 404 due to the obstruction of the floor-mounted conventional treatment couch 106 and the floor-mounted LINAC 106. Alternatively, other obstructions may cause the LINAC 103 to have unreachable surface areas. In one embodiment, the unreachable surface area 404 may be caused by the robot-based LINAC 103 being mounted to one side of the conventional treatment couch 106, as illustrated in FIG. 4B. FIG. 4B includes a two-dimensional circular shape of the total usable surface area 404 and the unreachable surface area 405. It should be noted that although represented as a two-dimensional circular shape in FIG. 4B, the total usable surface area 404 may be the surface area of an approximate spherical shape. Alternatively, other usable surface areas may be used of different shapes that have been obtained by varying the SAD.

Figure 4C:
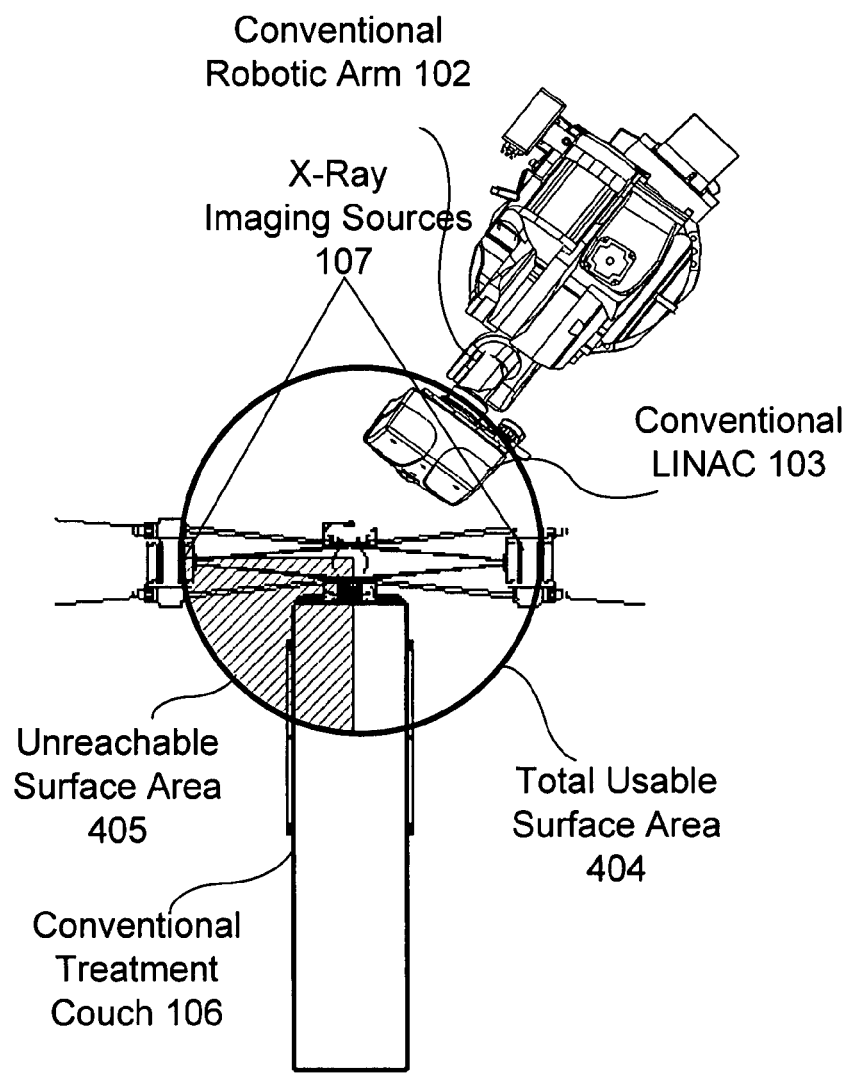
FIG. 4C illustrates a top-down view of a total usable surface area of a conventional treatment couch and a conventional LINAC disposed on a second side of the conventional treatment couch.

It should be noted that the unreachable area 404 can not be cured by merely mounting the robotic arm of the robot-based LINAC 203 on the opposite side of the conventional treatment couch 106, as illustrated in FIG. 4C. FIG. 4C illustrates a top-down view of the total usable surface area 404 of the LINAC 103 having the robotic arm 102 of the robot-based LINAC 103 mounted to a second side of the conventional treatment couch 106. In this embodiment, the unreachable surface area 405 remains due to the obstruction of the conventional treatment couch 106 and the robotic arm 102 of the robot-based LINAC 103. In other words, merely mounting the robot-based radiosurgery system on another side does not overcome the positioning restriction due to the obstruction causing the unreachable area 405.

Figure 4D:
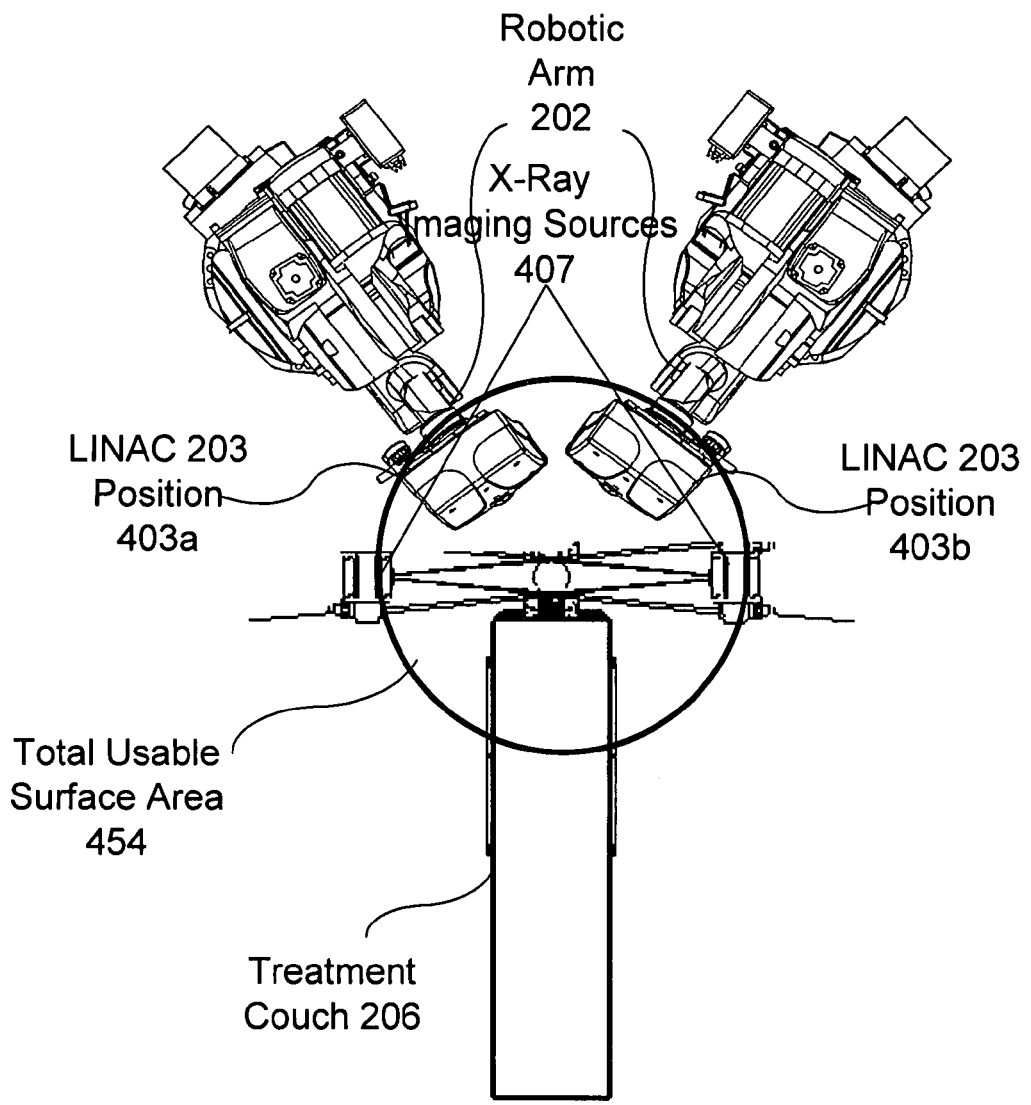
FIG. 4D illustrates a top-down view of a total usable surface area of one embodiment of the LINAC and the treatment couch of FIG. 4A.

FIG. 4D illustrates a top-down view of a total usable surface area 454 of one embodiment of the LINAC 203 and the treatment couch 206 of FIG. 4A. In this embodiment, the LINAC 203 is coupled to the robotic arm 202 and the treatment couch 206 is coupled to the robotic arm 402, as described above with respect to FIG. 4A. The details of the LINAC 203, treatment couch 206, and robotic arms 202 and 402 have been described herein, and are not repeated here as to not obscure the discussion of increasing the total usable surface area 454. The robot-based LINAC 203 is mounted to the floor on any side of LINAC 203. In this embodiment, the robot-based LINAC 203 is mounted on the first side of the treatment couch 206 at position 403a. As described above, the LINAC 203 may be positioned using the robotic arm 202 (e.g., articulated robotic arm) in a 3D workspace within the mechanical range of motion of the robotic arm 202. The LINAC 203 may be positioned to be a certain distance, the SAD, from the treatment target of the patient on the LINAC 203. Since the robot-based LINAC 203 may be positioned and oriented within the 3-D workspace using the robotic arm 202 of the robot-based LINAC 203, the LINAC 203 has a total usable surface area 454, which may be dependant upon the SAD. In one embodiment, if the SAD is a fixed number, the total usable surface area 454 would have approximate spherical shape. Alternatively, other usable surface areas may be used of different shapes that have been obtained by varying the SAD.

The total usable surface area 454 may represent the positions or nodes in which the LINAC 203 (e.g., x-ray LINAC) may be positioned to emit radiation to the treatment target of the patient. The total usable surface area 454, unlike the total usable surface area 404, is not limited by positioning restrictions as described above. Using the robotic arm 202, the positioning restrictions may be reduced or eliminated. Alternatively, using the robotic arms 202 and 402, the positioning restrictions may be reduced or eliminated.

As described above, the positioning restriction may be caused by treatment table or couch. In this embodiment, however, the LINAC 203 and the robotic arm 202 may be positioned to eliminate the unreachable area 405 as described and illustrated with respect to FIGS. 4C and 4D. FIG. 4D illustrates the second position 403b of the LINAC 203 with respect to the treatment couch 206. In this embodiment, the position of the LINAC 203 is shifted from position 403a to 403b. It should be noted that the LINAC 203 has not been remounted to the second side, as illustrated in FIG. 4C, but has been moved by the robotic arm 202. In other words, the LINAC 203 coupled to the robotic arm 202 may increase the total usable surface area 454 that the LINAC 203 may be positioned for emitting radiation to the treatment target of the patient. Alternatively, other movements may be used to eliminate the unreachable surface area and to increase the total usable surface area 454 of FIG. 4D. For example, in another embodiment, the LINAC 203 and the robotic arm 202, as well as the treatment couch 206 and the robotic arm 402 can be positioned to eliminate the unreachable area 405 as described and illustrated with respect to FIGS. 4C and 4D.

FIG. 4D includes a two-dimensional circular shape of the total usable surface area 454. It should be noted that although represented as a two-dimensional circular shape in FIG. 4B, the total usable surface area 454 may be the surface area of an approximate spherical shape. Alternatively, other usable surface areas may be used of different shapes that have been obtained by varying the SAD.

In another embodiment, the obstruction may be caused by the ground; thus, when using a conventional treatment couch 106, the obstruction creates an unreachable surface area on a bottom portion of an approximately spherical usable area. Using a vertically mounted robotic arm 202, the LINAC 203 may be raised up from the floor from a first position to a second, higher position, eliminating the unreachable surface area and increasing the total usable surface area. Alternatively, other unreachable surface areas may be overcome by coordinating the movement of the robotic arm 202 and the LINAC 203, such as, for example, obstructions due to the detectors 408, and x-ray imaging sources 407. In another embodiment, the movement of the robotic arm 202 and the LINAC 203 are used in posterior treatments that were unreachable using the conventional robotic arms. Alternatively, the movement of the robotic arm 202 and the LINAC 203 may be used in other positions and orientations, and in other types of treatments.

In the embodiments described above, the LINAC 203 and robotic arm 202, and the treatment couch 206 and robotic arm 402 are vertically mounted. Alternatively, a floor or ceiling mounted robotic arms may be used.

Although the embodiments above are described as moving the LINAC 203 and robotic arm 202 with respect to the treatment couch 206, which is coupled to a robotic arm 402, to reduce or eliminate unreachable area 405 to increase the total useable surface area 545, in other embodiments, the LINAC 203 and robotic arm 202 are moved with respect to a conventional treatment couch 106, which may be coupled to a conventional robotic arm, such as robotic arm 102, or a conventional treatment couch that is not coupled to a conventional robotic arm, to reduce or eliminate unreachable area 405 to increase the total useable surface area 545.

It should be also be noted that using the embodiments described herein, the robotic arm can position the LINAC 203 in symmetrical position with respect to the treatment couch 206, such as described in FIGS. 2I and 2J, as well as FIG. 4D. As described above, moving the LINAC 203 into symmetrical positions may lead to simplified paths for path planning and contact avoidance, and may increase the workspace by increasing the number of nodes at which the LINAC 203 can be positioned and oriented to direct radiation to a target.

Figure 1B:
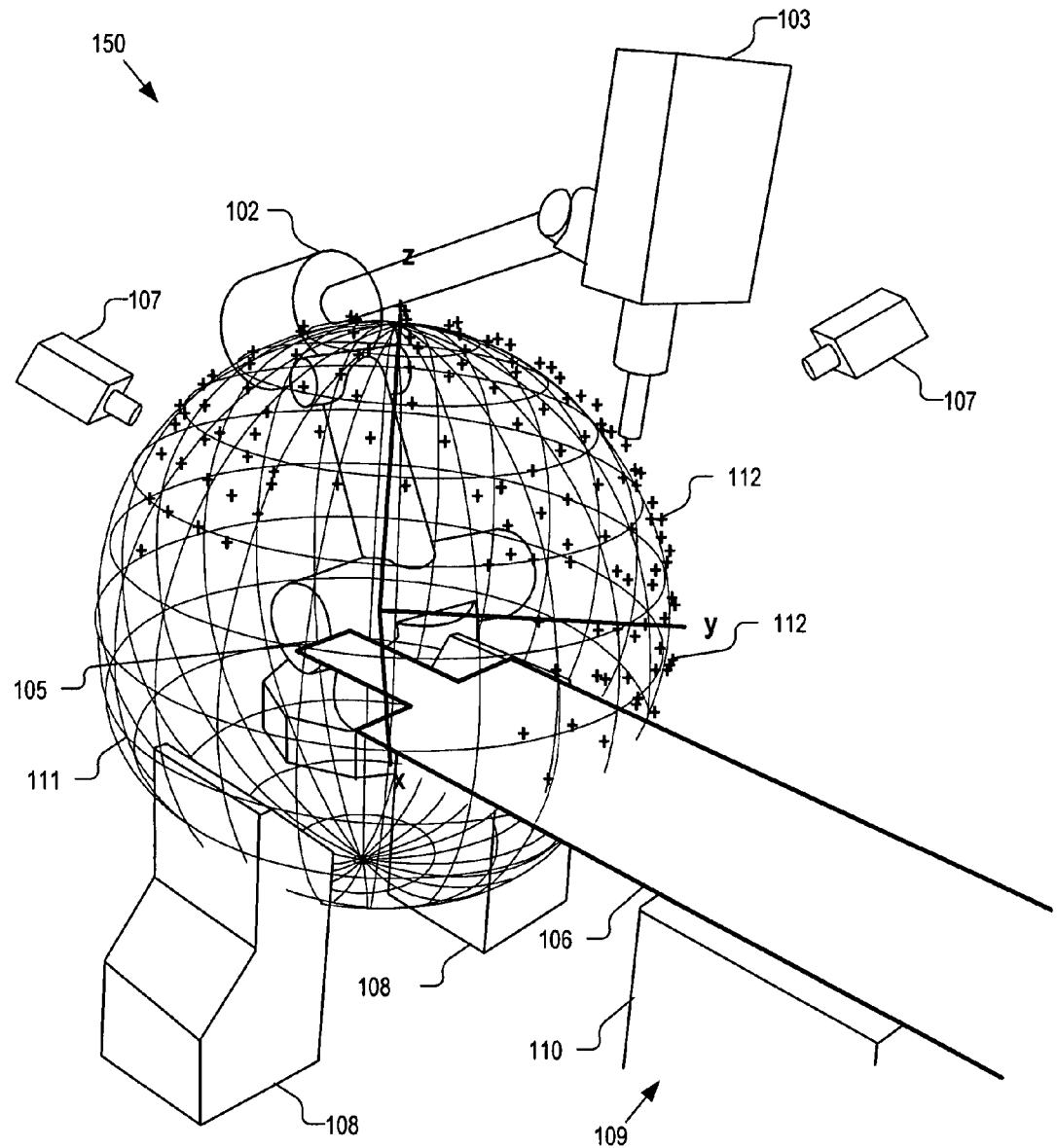
FIG. 1B is a perspective drawing illustrating a workspace of a conventional radiation treatment system including a set of spatial nodes at which to position the radiation source.
Figure 4E:
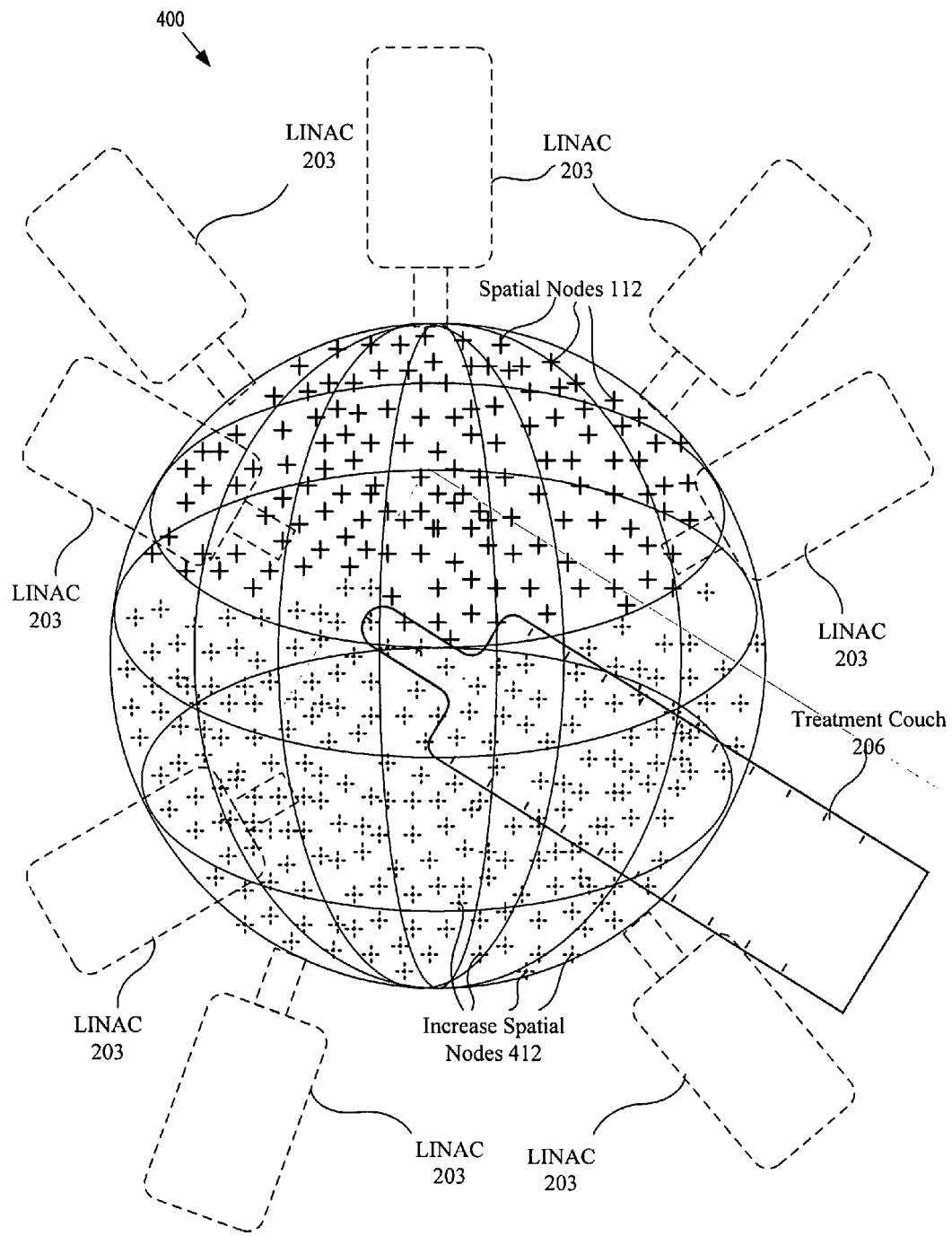
FIG. 4E is a perspective drawing illustrating a workspace of the system that includes the robotic treatment delivery system of FIG. 2A.

FIG. 4E is a perspective drawing illustrating a workspace 411 of the system 400 that includes the robotic treatment delivery system 200 of FIG. 2A. The workspace 411 includes a set of spatial nodes 112 at which to position the radiation source, similar to the spatial nodes 112 of the conventional system of FIG. 1B. Each of the spatial nodes 112 are represented by a "+" symbol (only a couple are labeled). A workspace or node set, as described above, is a collection of spatial nodes and associated safe paths interconnecting these spatial nodes. However, unlike the workspace of conventional systems (e.g., workspace 111), the workspace 411 and the number of spatial nodes may be increased using the robotic arm 202. As such, the workspace 411 also includes a set of additional or increased spatial nodes 412, as illustrated as dashed "+" in FIG. 4E. The total number of spatial nodes 112 and increased spatial nodes 412 of the workspace 411 is greater than the total number of spatial nodes 112 of the workspace 111 of the conventional system of FIG. 1B.

By moving the LINAC 203 using the robotic arm 202, the LINAC 203 may access certain zones (e.g., spatial nodes) around the treatment couch 206 that were previously blocked or otherwise unreachable in conventional systems. For example, the conventional robotic arm could not position the LINAC 103 around the treatment couch 106 to position the LINAC 103 in certain positions, as illustrated in the workspace 111 of FIG. 1B. These blocked positions, however, are not blocked and are reachable for the treatment delivery system 200, as described herein. Having greater accessibility to those certain zones, which were previously blocked or otherwise unreachable by the treatment couch in conventional systems, increases the workspace 411 (e.g., spatial nodes at which the LINAC 203 may deliver radiation to the target).

It should be noted that although workspace 411 is spherical, alternatively, the workspace 411 may have other geometries (e.g., elliptical) and defined for VOIs residing in the head of a patient, or within other areas of a patient. Additionally, multiple workspaces may be defined for different portions of a patient, each having different radius or SADs, such as 650 mm and 800 mm. The SAD is the distance between the collimator in the LINAC 203 and the target within the VOI.

The SAD defines the surface area of the workspace. In one embodiment of an elliptical workspace, the SAD may range from 900 mm to 1000 mm. Other SADs may be used.

Spatial nodes 112 and increase spatial nodes 412 reside on the surface of workspace 411. Spatial nodes represent positions where the LINAC 203 is pre-programmed to stop and delivery a dose of radiation to the VOI within the patient. During delivery of a treatment plan, robotic arm 202 moves the LINAC 203 to each and every spatial node 112 and 412, where a dose is determined to be delivered, following a pre-defined path. The predefine path may also includes some spatial nodes 112 and 412 where no dose needs to be delivered, in order to simplify the motions of the robotic arm 202.

The node set may include spatial nodes that are substantially uniformly distributed over the geometric surface of workspace 411. The node set includes all programmed spatial nodes 112 and 412 and provides a workable number of spatial nodes 112 and 412 for effectively computing treatment plan solutions for most ailments and associated VOIs. The node set provides a reasonably large number of spatial nodes 112 and 412 such that homogeneity and conformality thresholds can be achieved for a large variety of different VOIs, while providing enough vantage points to avoid critical structures within patients. It should be appreciated that the node set may include more or less spatial nodes 112 and 412 than is illustrated or discussed. For example, as processing power increases and experience gained creating treatment plans, the average number of spatial nodes 112 and 412 may increase with time to provide greater flexibility and higher quality treatment plans.

During radiation treatment, the patient rests on treatment couch 206, which is maneuvered to position a volume of interest ("VOI") containing a target to a preset position or within an operating range accessible to radiation source of the LINAC 203. The robotic arm 202 has multiple (e.g., five, six, seven, or more) DOF capable of positioning the LINAC 203 with almost an infinite number of positions and orientations within its operating envelope.

Figure 5:
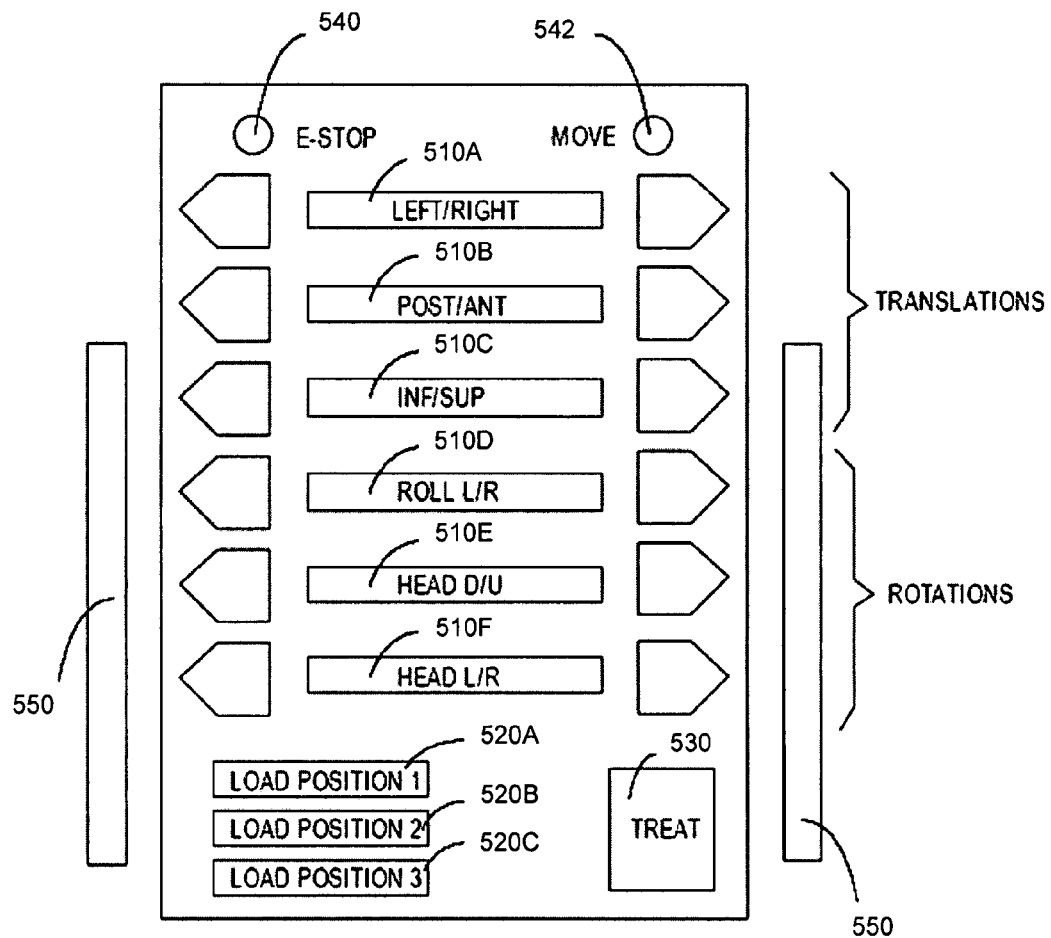
FIG. 5 illustrates one embodiment of a schematic diagram of a handheld user interface unit.

FIG. 5 illustrates one embodiment of a schematic diagram of a handheld user interface unit. The user interface unit 500 may affect computer control of the at least four rotational DOF and one substantially vertical, linear DOF of the robot-controlled LINAC 203. In an exemplary embodiment, the user interface unit 500 includes: a bus interface for connecting the LINAC 203 to the treatment system primary workstation including the controller 201, sensor system, imaging system, robotic arm 202, the robotic arm 402, treatment couch 206; at least one user interface unit, such as user interface unit 500 for allowing the user to interface with the controller 201 to interactively control the motion of the either or both the robot-based LINAC 203 or the robot-based treatment couch 206; and a hardware interface to the treatment system E-stop (emergency stop) circuitry. The bus interface may be an Ethernet bus interface that can be connected to the treatment system primary workstation. The hardware interface to the E-stop circuitry may disable computer-controlled motions of the robotic treatment delivery system 200 when any E-stop is engaged.

The E-stop mechanism may be operable to stop computer-controlled motion of the robotic treatment delivery system 200 or the robot-based patient positioning system 401. In one embodiment, the "System E-stop" may be an emergency lockout mechanism, capable of shutting down any and all radiation, and any and all motion. In other words, the "System E-stop" may shut down at least one of the following: 1) generation of therapeutic x-ray beams by the LINAC 203; 2) any motion of the treatment couch 206 and/or the robotic arm 402; 3) any motion of the LINAC 203 and/or the robotic arm 202; and 4) the imaging system.

The user interface unit 500 may allow the user or operator to interactively participate in controlling the motion of the robotic arm 202 and the LINAC 203, by implementing one or more user-selectable functions. The user interface unit 500 may also allow the user or operator to interactively participate in controlling the motion of the robotic arm 402 and the treatment couch 206, by implementing one or more user-selectable functions. In one embodiment, the user interface unit 500 may be a remote control unit. Alternatively, the user interface unit may be a graphical user interface unit, as described below. These user-selectable functions may include, but are not limited to, the following: 1) a function that allows the user to power on the LINAC 203, so that the acquisition of the position of the LINAC 203 can be initiated; 2) a function that allows the user to activate the x-ray imaging system 107, so that the acquisition of real time or near real time images of the target can be initiated; 3) a function for allowing the user to move the treatment couch 206 to one or more pre-programmed loading positions, which facilitates the loading of the patient onto the treatment couch 206 in a desired manner; 4) a function for allowing the user to move the LINAC 203 to a pre-programmed "TREAT" position, which may be the default treatment position; 5) a function for displaying to the user the translations and rotations corresponding to the LINAC 203 corrective motions needed to adjust the target position, in accordance with the information from the real time or near real time images; 6) a function for allowing the user to compare the translations and rotations with respective pre-specified limits for each translation and rotation; 7) a function for allowing the user to modify one or more of the pre-specified limits; and 8) a function for allowing the user to verify that the translations and rotations fall below the pre-specified limits, and thereupon activate the radiation source of the LINAC 203 to initiate treatment delivery.

In one exemplary embodiment, the user interface unit 500 may be a handheld remote control unit (e.g., handheld pendant) that provides a user with remote control capabilities for remote control of the motion of the robotic arm 202 and LINAC 203 and/or the motion of the robotic arm 402 and the treatment couch 206. User interface unit 500 of FIG. 5 may be a handheld pendant, and may include a number of button icons respectively associated with these user-selectable functions. The handheld remote control unit 500 may provide controls to manually adjust the patient's position or orientation with respect to the LINAC 203, and/or the position or orientation of the LINAC 203 with respect to the treatment couch 206, and status indicators related to the motions of the robotic treatment delivery system 200 or of the robot-based patient positioning system 401.

In the illustrated embodiment, the handheld remote control unit 500 includes motion switches: six sets of axes motion control switches 510A-510F, three loading position switches 520A, 520B, and 520C, and a treat switch 530. The axes motion control switches may provide bi-directional manual control of each DOF via a pushbutton. The axes motion control switches may cause movement of the desired axes (three rotational axes: left/right (510A), posterior/anterior (510B), inferior (towards the feet)/superior (towards the head) (510C); three rotational axes: roll left/right (510D); head down/up (510E); head left/right (510F)) in the desired direction, as long as the switch is held down and motion is disabled. The loading switches 520A, 520B, and 520C may each initiate a programmed motion, if motion is enabled, that causes the LINAC 203 to automatically move to the fully retracted, fully lowered loading position without any further operator action. The controller 201 may have one or more pre-programmed loading positions, and alternatively, a user may manually set a loading position for a patient through the handheld user interface unit 500 or a computer interface 600 illustrated in FIG. 6. The controller 201 may store the loading position for a particular patient for future treatment. The treat switch 530 may initiate a programmed motion, if motion is enabled, that causes the LINAC 203 to move to a position defined by the controller 201 and previously downloaded to the LINAC 203.

The remote control unit 500 may also include a pair of motion enable switches 550. Depressing one or both switches may enable all motion switches (axes motion control, loading positions, and treat), and overrides the System E-stop, if present, although it may not override any table E-stop switches. Releasing one or both of the enable switches while a programmed motion is occurring may cause that motion to stop.

The remote control unit 500 may also include a pair of status indicators 540 and 542, which may be light emitting diodes (LEDs) that provide an indication of whether motions are enabled and being accepted. In the illustrated embodiment, the E-stop LED 540 may be yellow when System E-stop is asserted, green when overridden by enable switches, and off when no System E-stop is asserted. The MOVE LED 542 may be green whenever a switch is pushed and motion is enabled, flashing green when a programmed movement is occurring, and yellow when the table E-stop is engaged.

The remote control unit 500 may also include a GoTo switch (not shown), allowing the user to access stored locations. The remote control unit 500 may also include display capabilities (not shown), for example to display to the user the translations and rotations, or to display informational messages to the user. The remote control unit 500 may also include absolute and relative position display/input modes (not shown). In another embodiment, the remote control unit 500 may also include a switch for activating the sensor system 104 to initiate detecting the position of the LINAC 203.

Figure 6:
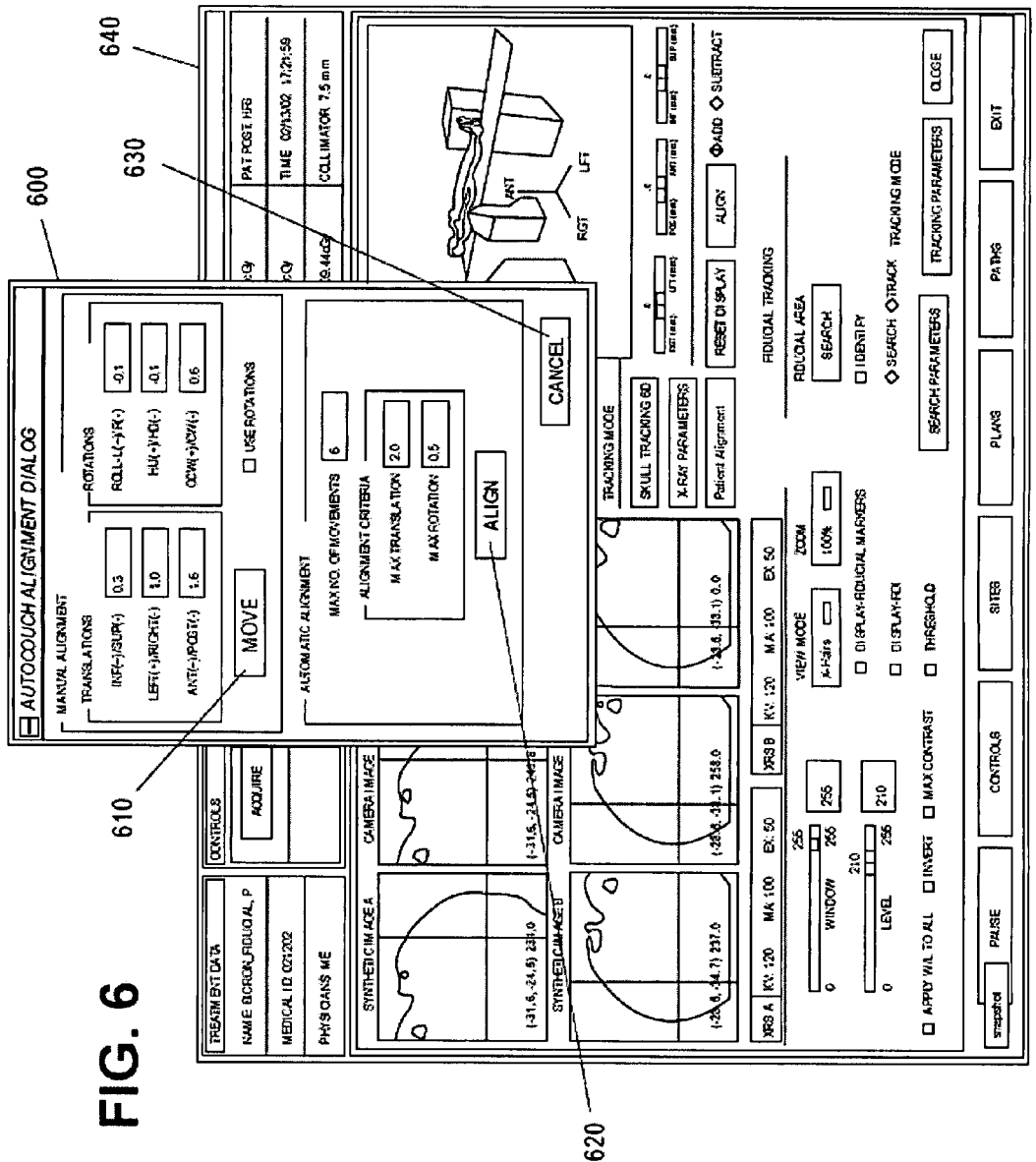
FIG. 6 illustrates an exemplary embodiment of a user interface screen, launched onto a treatment delivery display screen.

One or more user interface screens on the user control console of the primary CyberKnife® workstation, may allow the user to inspect, initiate, and interactively control the motion of the robotic treatment delivery system 200 for positioning the LINAC 203. FIG. 6 illustrates an exemplary embodiment of a user interface screen 600, launched into a treatment delivery screen 640 of the primary workstation. In the illustrated embodiment, the user interface screen 600 may provide to the user an integrated patient treatment couch position display, and patient treatment couch motion control capabilities, as well as LINAC position display and LINAC motion control capabilities. The user interface screen 600 provides sub-options to adjust translations only, or rotations only or all DOF available together.

In one embodiment, the user interface screen 600 includes button icons that allow the user to activate the sensor system 104 to detect the position of the LINAC 203.

In the illustrated embodiment, an ALIGN COUCH button in the treatment delivery screen 640 may launch the user interface screen 600. The user interface screen 600 may include a number of fields, with different functions. These fields may include translation and rotation fields, which are initially filled with the corrective motions of the robotic treatment delivery system 200 returned by the TLS unit of the controller 201. If no valid corrective motions are available, these fields are left blank. The translation and rotation fields may be editable.

In the illustrated embodiment, the user interface screen 600 includes a MOVE button 610, an "AUTO ALIGN" button 320, and a "CANCEL" button 630. The "MOVE" button 610 moves the LINAC 203 by the amount of translations and rotations indicated. If the "Apply rotation" field is unchecked, the LINAC 203 may be moved only in rotational axes. The "AUTO ALIGN" button 620 initially moves the LINAC 203 by the amount of translations and rotations indicated, and proceeds to acquire images through the imaging system and correct LINAC 203 positions automatically until pre-specified "Auto align limits" are satisfied. This may mean that the translations and rotations are below the pre-specified limits, or the number of images indicated is taken. The "Auto align limits" fields are filled in from a system configuration file, but can be edited. The "CANCEL" button 630 will return to the Patient Alignment interface.

In one embodiment, the user interface screen 600 includes button icons that allow the user to adjust imaging parameters, such as the intensity, energy, and duration of the x-rays in the imaging beams generated by the imaging system 107; the number of real time or near real time images to be acquired; the selection and de-selection of fiducials; and rigid body parameters.

In operation, an approximate treatment location for the patient may be computed, as part of the treatment planning process. When the treatment plan is loaded into the controller 201, the approximate treatment location may be downloaded into the LINAC 203. The operator positions the patient on the LINAC 203, and applies any restraining devices. The operator then presses the "TREAT" button in the handheld user interface unit 500 (shown in FIG. 5), and the LINAC 203 automatically moves to bring all of its DOF to the stored positions. Alternatively, the "Treat" command could also be issued from the user interface screen 600. The number of axes to move simultaneously may be limited by design to ensure that power demands are not excessive and that the patient is comfortable with the number of simultaneous motions taking place.

The operator then exits the treatment room and using the user interface screen 600 (shown in FIG. 6) on the workstation or dedicated control panel, may command the system to align the patient to within desired tolerances. The user interface screen 600 may allow the user to enter parameters such as the maximum number of real time or near real time images to take during the alignment process, and the desired tolerances for position and orientation. The user interface screen 600 also may allow the errors associated with each image to be displayed.

After obtaining a satisfactory alignment, the therapeutic radiation treatment system 106 may be commanded to begin treatment. As part of the treatment, real time or near real time images may be obtained periodically by the imaging system 107, to check whether the patient moves during the treatment. If the patient does move, the treatment delivery can be paused automatically or manually by the operator, and the patient can be realigned, by effecting appropriate corrective motions of the robotic treatment delivery system 200 or of the patient positioning system 401. At the conclusion of the treatment, the operator reenters the treatment room and uses the "Load Position" buttons on the handheld user interface unit 500 to return the LINAC 203 to the loading/unloading position for patient unloading. Alternatively, the system may issue the command to return to the original loading position from the user interface screen 600.

In one embodiment, components of the robotic arm 202 or robotic arm 302 may include touch-sensing material on the components' exterior. In another embodiment, the exterior of the components may be coated with contact foam. Alternatively, other materials may be used to prevent components of the robotic arm 202 or of robotic arm 302 from crushing or knocking over the operator. Specific details regarding the touch-sensing material and contact foam that are known to those of ordinary skill in the art have not been included as to not obscure the discussion regarding coating the exterior of the robotic arms 202 and 402 with material to prevent the operator from being knocked over or crushed by the robotic arms.

Following is a more detailed description of another embodiment of operation of the robotic treatment delivery system described above.

The first stage is the initial patient set-up stage. During this stage, the treatment planning files are downloaded, prior to patient entry into the treatment room. During the download of treatment files, the treatment position of the LINAC 203 and/or treatment couch 206 may be downloaded into the controller 201. The treatment position of the LINAC 203 and/or treatment couch 206 may be one of: a) a default position for the beam path set selected; and b) a treatment position for the patient, the last time the same plan was used. Before the patient walks into the treatment room, one of the loading position buttons on the handheld remote control unit 500 may be pressed, so as to position the treatment couch 206 in a pre-defined comfortable position for the patient to get onto the treatment couch 206. The patient may be then immobilized, for example using a thermoplastic mask and or other immobilization devices.

The "TREAT" button on the handheld remote control unit 500 may be used to position the LINAC 203 and/or treatment couch 206 to the nominal treatment position. For head or body treatments, or if this is a second or subsequent treatments for the patient with the same plan, the nominal treatment position may be adequate for further automatic positioning, and the operator can proceed to the user control console for automatic positioning of the patient and/or the LINAC 203. Otherwise, the LINAC 203 and/or treatment couch 206 may be further manually adjusted, using the handheld remote control unit 500, so that the anatomical target region of interest may be within the imaging field of view. The operator then proceeds to the user interface screen 600, for automatic positioning of the patient and/or the LINAC 203.

The next stage may be the initial image acquisition stage. During this stage, the operator may acquire images, using the ACQUIRE button on the patient alignment screen in the user interface screen 600 (shown in FIG. 6). If necessary, imaging parameters may need to be adjusted. Some examples of these parameters are: x-ray parameters; de-selection of fiducials that may have migrated or otherwise difficult to track; and adjustment of rigid body parameters.

The next stage may be the one-time alignment stage of the LINAC 203 and/or treatment couch 206. The user selects the "AUTO COUCH" button on the patient alignment screen. This brings up a Couch Adjustment interface screen of user interface screen 600, which contains the initial corrections obtained from the TLS unit of the controller 201. The initial corrections from TLS may be editable. The "MOVE" button moves the treatment couch 206 by the amount of corrections indicated in the window. A similar button may be used to move the LINAC 203 by the amount of corrections indicated in the window of the interface screen. The option to disable rotation corrections may also be available. The "AUTO ALIGN" button may perform the first correction, and proceeds to complete the automatic alignment.

The next stage may be the automatic alignment stage of the LINAC 203 and/or treatment couch 206. The "AUTO ALIGN" button in the interface screen may perform the automatic alignment. Auto Align may start by making the initial corrections, and proceeds to take additional images and perform the correction from the image, until one of the following conditions are met: the desired number of images in the Auto Alignment phase is acquired, and/or the residual corrections fall below the limits specified in the Auto Alignment interface.

The next stage may be the patient re-alignment stage. Patient re-alignment may be entered whenever the system encounters a recoverable error (including operator pause), and the system is resumed from this state. Patient re-alignment may be handled the same way as patient alignment. In other words, after the initial acquisition, further adjustments can be done automatically using the "AUTO ALIGN" button in the interface.

The final stage may be the treatment delivery stage. Treatment delivery may be initiated when the corrective motions for the LINAC 203 fall below pre-specified limits for translations and rotations of the robotic arm 202 and LINAC 203. The corrective motions downloaded to the controller 201 of the robotic treatment delivery system 200 may include translations and the specified set of rotations. The robot may move to the nominal position for the node, correct by the specified translation and rotation, and then enable the x-ray beam generator of the therapeutic radiation treatment system 106. At the end of dose delivery for the node, the robot of the therapeutic radiation treatment system 106 may proceed to the next node in this nominal position.

The controller 201 may include software for error detection, reporting, and correction. In one embodiment, the error handling software includes "operator pause" functionality. This functionality allows the user to stop image acquisition, if one is in progress, and return to a target alignment or realignment mode. The user may also stop the motion of the robotic treatment delivery system 200, if one is in progress, and return to the target alignment/realignment mode. The user may also stop subsequent image acquisitions and motions of the robotic treatment delivery system 200, if the "auto alignment" mode is in progress.

In one embodiment, the error handling software also includes functionality for handling TLS (target locating system) errors. Appropriate TLS errors, such as soft algorithm errors, and/or E-stop for hardware errors, are reported. Upon acknowledgement of the error, the controller 201 may return to the alignment or re-alignment state. The user may stop subsequent image acquisitions and motions of the robotic treatment delivery system 200, if "auto alignment" is in progress. During the initial alignment, the "patient out of bounds" error may be disabled, but the "TREAT" button may be disabled until the patient is within bounds.

In one embodiment, the error handling software includes functionality for handling interface errors. The interface errors such as communication errors are handled as soft errors, which require user acknowledgment, but do not engage an E-stop. In one embodiment, the error handling software may include functionality for handling E-stops. In this embodiment, an E-stop stops computer-controlled motion of the robotic treatment delivery system 200, using a dual redundant mechanism. The controller software stops generating any further motion command signals. The LINAC 203 controller hardware may be disabled from LINAC 203 movement when an E-stop is engaged. Even when the E-stop is engaged, the LINAC 203 may be capable of moving using the handheld user interface unit 500. On resumption from pause or a recoverable E-stop, the E-stop may be cleared by system reset from the operator console, which then goes into a patient re-alignment state. At this stage, the user can use auto-align to refine the patient position. The "RESUME" button on the patient re-alignment screen enables resumption of treatment delivery.

Figure 7:
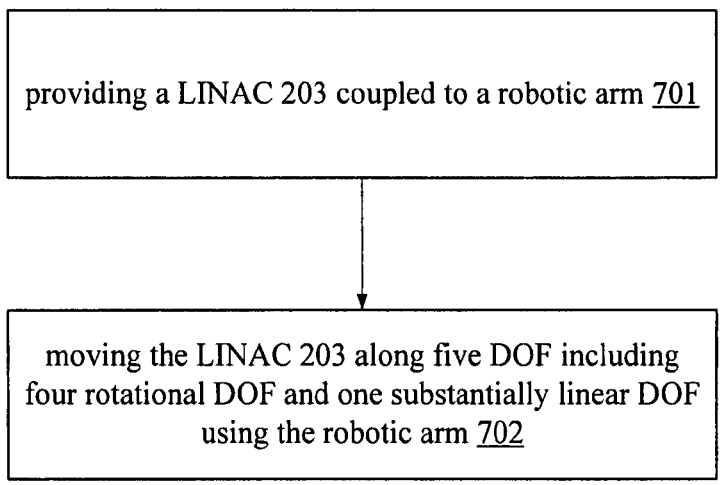
FIG. 7 illustrates a one embodiment of a method for positioning a LINAC using a robotic arm.

FIG. 7 illustrates a one embodiment of a method for positioning a LINAC using a robotic arm. The method may include providing a LINAC 203 coupled to a robotic arm (e.g., 202 or 302), operation 701, and moving the LINAC 203 along five DOF including four rotational DOF and one substantially linear DOF using the robotic arm, operation 702. Moving the LINAC 203 along five DOF includes moving the LINAC 203 in one rotational axis for translational movement of the LINAC 203 along mutually orthogonal horizontal coordinate x- and y-axes, moving the LINAC 203 in three rotational axes for roll-, pitch-, and yaw-rotational movements about an x-axis, a y-axis, and a z-axis, respectively. Moving the LINAC 203 along the five DOF may also include moving the LINAC along a substantially vertical, linear DOF having a substantially linear axis for translational movements of the LINAC along a substantially vertical line in a z-axis that is substantially perpendicular to horizontal coordinate x- and y-axes. Alternatively, moving the LINAC 203 along the five DOF may also include moving the LINAC along a substantially horizontal, linear DOF having a substantially linear axis for translational movements of the LINAC along a horizontal line in the mutually orthogonal horizontal coordinate x- and y-axes that is substantially perpendicular to the z-axis.

In another embodiment, the method includes moving the LINAC 203 along six DOF including five rotational DOF and one substantially linear DOF using the robotic arm moving the LINAC 203. In one embodiment, the five rotational DOF include two horizontal rotational axes (Axes 3, and 2 of FIG. 2A) (e.g., x-, y-axes) and three rotational axes including a yaw axis, a pitch axis, and a roll axis (Axes 6, 5, and 4 of FIG. 2A), and the one substantially vertical, linear DOF includes a substantially linear axis for translational movement of the LINAC 203 along a substantially vertical line in a coordinate axis (Axis 1 of FIG. 2A) (e.g., z-axis) substantially perpendicular to the two horizontal coordinate axes (e.g., x-, and y-axes).

In another embodiment, the method for positioning the LINAC 203 includes moving the LINAC 203 along seven DOF including six rotational DOF and one substantially linear DOF using the robotic arm. In one embodiment, the six rotational DOF include three rotational axes (e.g., x-, y-, z-axes) and three rotational axes including a yaw axis, a pitch axis, and a roll axis (e.g., roll-, pitch-, and yaw-axes), and the one substantially vertical, linear DOF includes a substantially linear axis for translational movement of the LINAC 203 along a substantially vertical line in a coordinate axis (e.g., z-axis) substantially perpendicular to the two horizontal coordinate axes (e.g., x-, and y-axes) or along a substantially horizontal line in the two horizontal coordinate axes (e.g., x-, and y-axes) perpendicular to the vertical coordinate axis (e.g., z-axis).

In another embodiment, the method for positioning a LINAC 203 using a robotic arm 202 may include providing a LINAC 203 coupled to a robotic arm 202, and moving the LINAC 203 along six rotational DOF and one substantially vertical, linear DOF using a robotic arm 202. In one embodiment, the six rotational DOF include three rotational axes (Axes 3, 2, and 1 of FIG. 3) (e.g., x-, y-, & z-) and three rotational axes including a yaw axis, a pitch axis, and a roll axis (Axes 6, 5, and 4 of FIG. 3), and the one substantially vertical, linear DOF includes a substantially linear axis for translational movement of the LINAC 203 along a substan-tially vertical line in a coordinate axis (e.g., z-axis) substantially perpendicular to the two horizontal coordinate axes (e.g., x-, and y-axes).

The method may further include moving the LINAC 203 along a single one of the rotational axes and the rotational axes without moving the LINAC 203 along a different one said axis throughout an entire range of motion of the LINAC 203. The method may also include providing a controller for moving the robotic arm and LINAC 203 along four, five, or six rotational DOF and one substantially vertical, linear DOF. The method may also include providing a user interface unit coupled to the controller for manually moving the robotic arm and LINAC 203 along at least one of four rotational DOF and one substantially linear DOF (e.g., vertical or horizontal).

In one embodiment, moving the LINAC 203 along five rotational DOF and one substantially vertical, linear DOF using the robotic arm includes rotating the LINAC 203 along the yaw-axis using a tool-yaw joint of the robotic arm, rotating the LINAC 203 along the pitch-axis using a tool-pitch joint of the robotic arm, rotating the LINAC 203 along the roll-axis using a tool-roll joint of the robotic arm, rotating the LINAC 203 along the two horizontal rotational axes using a elbow joint and a shoulder joint, and translating the LINAC 203 along a substantially vertical, linear axis using a track and track mount assembly perpendicular to the two horizontal rotational axes. In another embodiment, moving the LINAC 203 further includes rotating the LINAC 203 along an additional translational axis using an additional shoulder joint, totaling six rotational DOF and one substantially vertical, linear DOF. The six DOF may include three rotational axes for translational movements along mutually orthogonal x-, y-, and z-coordinate axes; and three rotational axes for roll-, pitch-, and yaw-rotational movements about x-, y-, and z-axes, respectively. The one substantially vertical, linear DOF may include a substantially linear axis for translation along a substantially vertical line in a z-coordinate axis perpendicular to the horizontal, x-, and y-coordinate axes.

Figure 8:
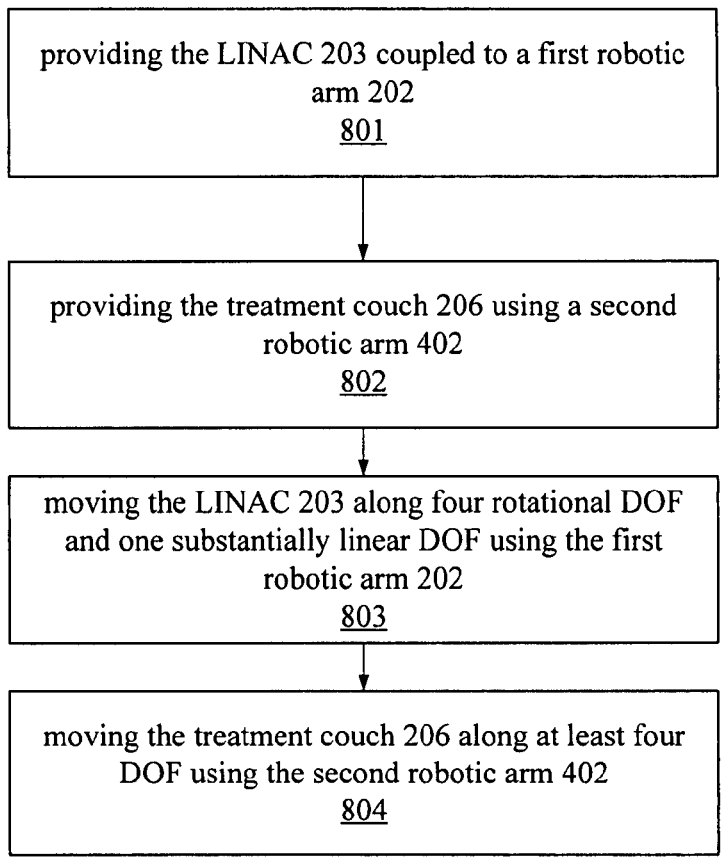
FIG. 8 illustrates another embodiment of a method for positioning a LINAC using a first robotic arm and a treatment couch using a second robotic arm.

FIG. 8 illustrates another embodiment of a method for positioning a LINAC 203 using a first robotic arm 202 and a treatment couch 206 using a second robotic arm 402. The method includes providing the LINAC 203 coupled to a first robotic arm 202, operation 801; providing the treatment couch 206 using a second robotic arm 402, operation 802; moving the LINAC 203 along four rotational DOF and one substantially linear DOF using the first robotic arm 202, operation 803; and moving the treatment couch 206 along at least four DOF using the second robotic arm 402, operation 804.

Moving the LINAC 203 along five DOF may include rotating the LINAC 203 along the z-axis using a tool-yaw joint of the first robotic arm 202, rotating the LINAC 203 along the y-axis using a tool-pitch joint of the first robotic arm 202, rotating the LINAC 203 along the x-axis using a tool-roll joint of the first robotic arm 202, rotating the LINAC 203 along the one or two horizontal rotational axes using an elbow joint or an elbow and a shoulder joint of the first robotic arm 202, and translating the LINAC 203 along a substantially linear axis using a first track in the first track mount assembly either in a horizontal linear axis or a vertical linear axis. Moving the treatment couch 206 along five DOF may include rotating the treatment couch 206 along the z-axis using a tool-yaw joint of the second robotic arm 402, rotating the treatment couch 206 along the y-axis using a tool-pitch joint of the second robotic arm 402, rotating the treatment couch 206 along the x-axis using a tool-roll joint of the second robotic arm 402, rotating the treatment couch 206 along the one or two horizontal rotational axes using an elbow joint or an elbow and a shoulder joint of the second robotic arm 402, and translating the treatment couch 206 along a substantially linear axis using a second track in the second track mount assembly either in a horizontal linear axis or a vertical linear axis.

In another embodiment, the method includes moving the LINAC 203 or the LINAC 203 and the treatment couch 206 in six DOF. In another embodiment, the method includes moving the LINAC 203 or the LINAC and the treatment couch 206 in seven DOF.

In another embodiment, the method includes providing a controller coupled to the LINAC 203 and the robotic arm 202 and the treatment couch 206 and the robotic arm 402. Alternatively, two separate controllers may be used to control the motions of the LINAC 203 using first robotic arm 202 and the treatment couch 206 using the second robotic arm 402. In another embodiment, the method includes providing an imaging system having an imaging field of view, and maintaining the LINAC 203 substantially outside of the imaging field of view for all supported treatment positions.

In one embodiment, moving the LINAC 203 and the robot-based LINAC 203 may include dynamically coordinating an orientation and position of the LINAC 203 and the treatment couch 206 using the controller 201. Dynamically coordinating the orientation and position of the LINAC 203 and the treatment couch 206 may increase a number of treatment targets within a mechanical range of motion of the robotic arm 202. In another embodiment, moving the LINAC 203 and the treatment couch 206 includes aligning a radiation source of the LINAC 203 with a treatment target within a patient disposed on the treatment couch 206. In another embodiment, moving the LINAC 203 and the treatment couch 206 further includes positioning the LINAC 203 and the treatment couch 206 to create a treatment target in a previously obstructed location within a mechanical range of motion of the robotic arm 202 and the LINAC 203.

In one embodiment, the previously obstructed location may be caused by an obstruction of a possible collision, for example, between either the LINAC 203, LINAC 203, their corresponding robotic arms with the robotic arm 202, the LINAC 203, the LINAC 203, x-ray imaging sources 407, detectors 408, and/or other components of the robot-based LINAC 203. Alternatively, the previously obstructed location may be caused by an obstruction of the radiation beam of the LINAC 203 with the robotic arm 202, the LINAC 203, the LINAC 203, x-ray imaging sources 407, detectors 408, and/or other components of the robot-based LINAC 203.

In one embodiment of positioning a patient location and orientation during medical operations includes positioning a treatment couch 206 along two horizontal rotational axes (x-, y-) (similar to Axes 2 and 3 of FIG. 2A) and three rotational axes (yaw, pitch, and roll) (similar to Axes 6, 5, and 4 of FIG. 2A); and positioning the treatment couch 206 along one substantially vertical, linear axis (z-) (similar to Axes 1 of FIG. 2A).

In another embodiment of positioning a patient location and orientation during medical operations includes positioning a treatment couch 206 along three rotational axes (x-, y-, z-)(similar to Axes 4, 3, and 2 of FIG. 3), and three rotational axes (yaw, pitch, and roll)(similar to Axes 7, 6, and 6 of FIG. 3); and positioning the treatment couch 206 along one substantially vertical, linear axis (z-)(similar to Axes 1 of FIG. 3). Although the robotic arms 202 and 402 are described as having similar number and types of DOF, the robotic arms 202 and 402 may include similar or dissimilar numbers of DOF, and similar or dissimilar types of DOF.

In one embodiment, the treatment couch 206 may be provided with an at least two directions loading mechanism, which, in operation, can load or unload the patient in horizontal manners and vertical manners. The robotic treatment delivery system 200 includes the treatment couch 206, which, in a vertical loading manner, may be positioned oblique to the horizontal plane, for example at approximately seventy degrees (70°) with respect to the horizontal plane. After the patient is secured on the treatment couch 206, the treatment couch 206 may position the patient to the treatment position within the workspace. In one embodiment, the top surface of the treatment couch 206 may be provided with a patient specific mold, which may be customized to fit the body curve of the patient. In another embodiment, one end of the treatment couch 206 may be provided with a footplate for supporting the patient's feet in vertical loading manners. In another embodiment, the treatment couch 206 may be provided with a chair-like supporting device, and the treatment couch 206 may be adapted to provide a sitting position for loading and/or unloading, and/or for treating the patient.

Alternatively, the treatment couch 206 may also provide loading/unloading positions, sitting loading/unloading positions, and other loading/unloading positions that are set for the convenience of particular patients.

It should be noted that more rotatable and/or slidable sections, for example, an additional arm, may be added to the robotic treatment delivery system 200 to obtain more flexibility and a greater reach of the LINAC 203. Alternatively, the robotic treatment delivery system 200 can include fewer sections than the robotic treatment delivery system 200, for example, including only an elbow assembly instead of both the elbow assembly and shoulder assembly. The translational and rotational movements of the robotic treatment delivery system 200 may be controlled manually and/or automatically by the computer controller 201.

Figure 9:
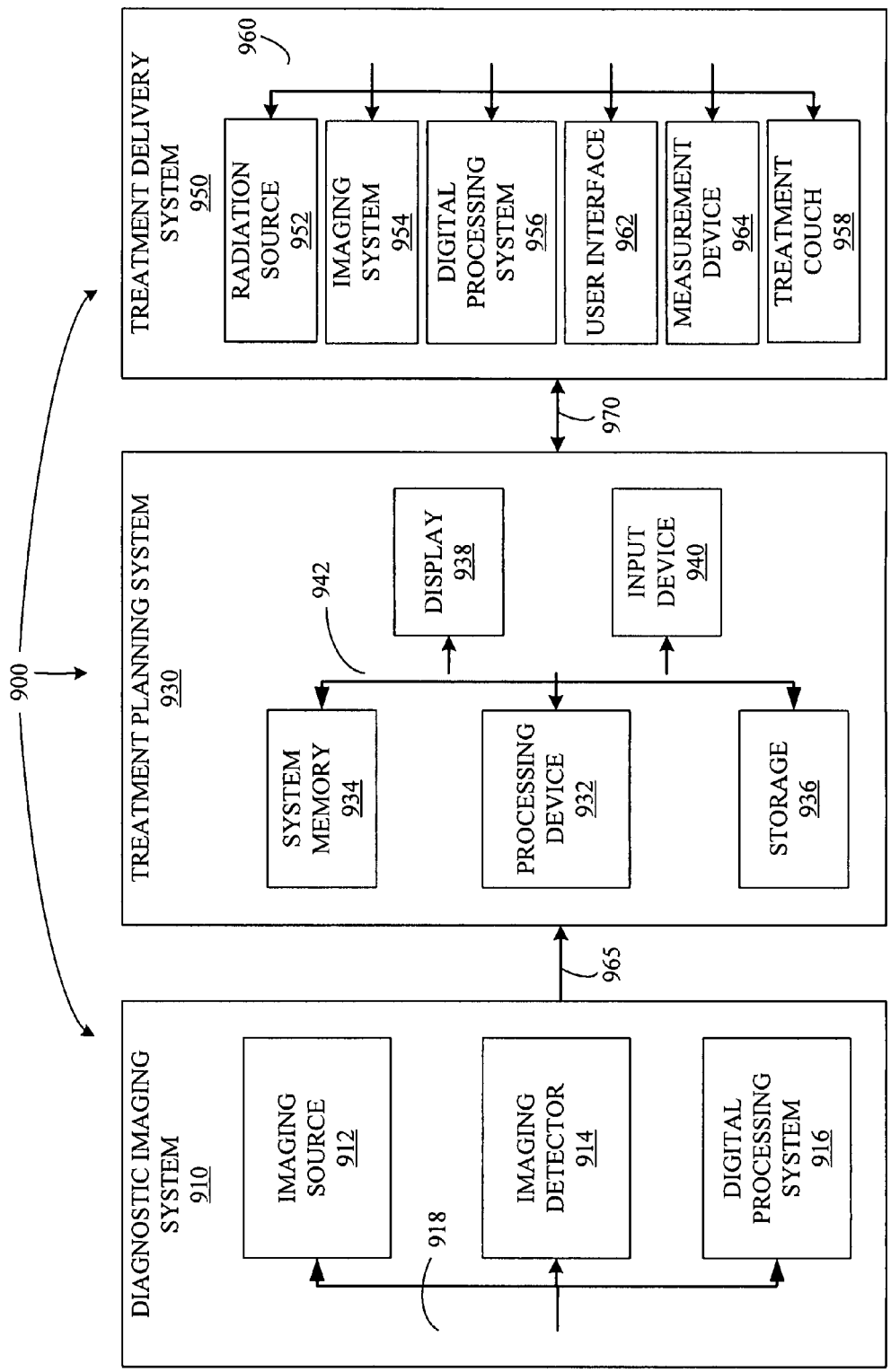
FIG. 9 illustrates a block diagram of one embodiment of a treatment system that may be used to perform radiation treatment in which embodiments of the present invention may be implemented.

FIG. 9 illustrates a block diagram of one embodiment of a treatment system 900 that may be used to perform radiation treatment in which embodiments of the present invention may be implemented. The depicted treatment system 900 includes a diagnostic imaging system 910, a treatment planning system 930, and a treatment delivery system 950. In other embodiments, the treatment system 900 may include fewer or more component systems.

The diagnostic imaging system 910 is representative of any system capable of producing medical diagnostic images of a volume of interest (VOI) in a patient, which images may be used for subsequent medical diagnosis, treatment planning, and/or treatment delivery. For example, the diagnostic imaging system 910 may be a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system such as a CT x-ray imaging system (or another particular system) is representative of the diagnostic imaging system 910, generally, and does not preclude other imaging modalities, unless noted otherwise.

The illustrated diagnostic imaging system 910 includes an imaging source 912, an imaging detector 914, and a digital processing system 916. The imaging source 912, imaging detector 914, and digital processing system 916 are coupled to one another via a communication channel 918 such as a bus. In one embodiment, the imaging source 912 generates an imaging beam (e.g., x-rays, ultrasonic waves, radio frequency waves, etc.) and the imaging detector 914 detects and receives the imaging beam. Alternatively, the imaging detector 914 may detect and receive a secondary imaging beam or an emission stimulated by the imaging beam from the imaging source (e.g., in an MRI or PET scan). In one embodiment, the diagnostic imaging system 910 may include two or more diagnostic imaging sources 912 and two or more corresponding imaging detectors 914. For example, two x-ray sources 912 may be disposed around a patient to be imaged, fixed at an angular separation from each other (e.g., 90 degrees, 45 degrees, etc.) and aimed through the patient toward corresponding imaging detectors 914, which may be diametrically opposed to the imaging sources 914. A single large imaging detector 914, or multiple imaging detectors 914, also may be illuminated by each x-ray imaging source 914. Alternatively, other numbers and configurations of imaging sources 912 and imaging detectors 914 may be used.

The imaging source 912 and the imaging detector 914 are coupled to the digital processing system 916 to control the imaging operations and process image data within the diagnostic imaging system 910. In one embodiment, the digital processing system 916 may communicate with the imaging source 912 and the imaging detector 914. Embodiments of the digital processing system 916 may include one or more general-purpose processors (e.g., a microprocessor), special purpose processors such as a digital signal processor (DSP), or other type of devices such as a controller or field programmable gate array (FPGA). The digital processing system 916 also may include other components (not shown) such as memory, storage devices, network adapters, and the like. In one embodiment, the digital processing system 916 generates digital diagnostic images in a standard format such as the Digital Imaging and Communications in Medicine (DICOM) format. In other embodiments, the digital processing system 916 may generate other standard or non-standard digital image formats.

Additionally, the digital processing system 916 may transmit diagnostic image files such as DICOM files to the treatment planning system 930 over a data link 960. In one embodiment, the data link 960 may be a direct link, a local area network (LAN) link, a wide area network (WAN) link such as the Internet, or another type of data link. Furthermore, the information transferred between the diagnostic imaging system 910 and the treatment planning system 930 may be either pulled or pushed across the data link 960, such as in a remote diagnosis or treatment planning configuration. For example, a user may utilize embodiments of the present invention to remotely diagnose or plan treatments despite the existence of a physical separation between the system user and the patient.

The illustrated treatment planning system 930 includes a processing device 932, a system memory device 934, an electronic data storage device 936, a display device 938, and an input device 940. The processing device 932, system memory 934, storage 936, display 938, and input device 940 may be coupled together by one or more communication channel 942 such as a bus.

The processing device 932 receives and processes image data. The processing device 932 also processes instructions and operations within the treatment planning system 930. In certain embodiments, the processing device 932 may include one or more general-purpose processors (e.g., a microprocessor), special purpose processors such as a digital signal processor (DSP), or other types of devices such as a controller or field programmable gate array (FPGA).

In particular, the processing device 932 may be configured to execute instructions for performing treatment operations discussed herein. For example, the processing device 932 may identify a non-linear path of movement of a target within a patient and develop a non-linear model of the non-linear path of movement. In another embodiment, the processing device 932 may develop the non-linear model based on a plurality of position points and a plurality of direction indicators. In another embodiment, the processing device 932 may generate a plurality of correlation models and select one of the plurality of models to derive a position of the target. Furthermore, the processing device 932 may facilitate other diagnosis, planning, and treatment operations related to the operations described herein.

In one embodiment, the system memory 934 may include random access memory (RAM) or other dynamic storage devices. As described above, the system memory 934 may be coupled to the processing device 932 by the communication channel 942. In one embodiment, the system memory 934 stores information and instructions to be executed by the processing device 932. The system memory 934 also may be used for storing temporary variables or other intermediate information during execution of instructions by the processing device 932. In another embodiment, the system memory 934 also may include a read only memory (ROM) or other static storage device for storing static information and instructions for the processing device 932.

In one embodiment, the storage 936 is representative of one or more mass storage devices (e.g., a magnetic disk drive, tape drive, optical disk drive, etc.) to store information and instructions. The storage 936 and/or the system memory 934 also may be referred to as machine readable media. In a specific embodiment, the storage 936 may store instructions to perform the modeling operations discussed herein. For example, the storage 936 may store instructions to acquire and store data points, acquire and store images, identify non-linear paths, develop linear and/or non-linear correlation models, and so forth. In another embodiment, the storage 936 may include one or more databases.

In one embodiment, the display 938 may be a cathode ray tube (CRT) display, a liquid crystal display (LCD), or another type of display device. The display 938 displays information (e.g., a two-dimensional or 3D representation of the VOI) to a user. The input device 940 may include one or more user interface devices such as a keyboard, mouse, trackball, or similar device. The input device(s) 940 may also be used to communicate directional information, to select commands for the processing device 932, to control cursor movements on the display 938, and so forth.

Although one embodiment of the treatment planning system 930 is described herein, the described treatment planning system 930 is only representative of an exemplary treatment planning system 930. Other embodiments of the treatment planning system 930 may have many different configurations and architectures and may include fewer or more components. For example, other embodiments may include multiple buses, such as a peripheral bus or a dedicated cache bus. Furthermore, the treatment planning system 930 also may include Medical Image Review and Import Tool (MIRIT) to support DICOM import so that images can be fused and targets delineated on different systems and then imported into the treatment planning system 930 for planning and dose calculations. In another embodiment, the treatment planning system 930 also may include expanded image fusion capabilities that allow a user to plan treatments and view dose distributions on any one of various imaging modalities such as MRI, CT, PET, and so forth. Furthermore, the treatment planning system 930 may include one or more features of convention treatment planning systems.

In one embodiment, the treatment planning system 930 may share a database on the storage 936 with the treatment delivery system 950 so that the treatment delivery system 950 may access the database prior to or during treatment delivery. The treatment planning system 930 may be linked to treatment delivery system 950 via a data link 970, which may be a direct link, a LAN link, or a WAN link, as discussed above with respect to data link 960. Where LAN, WAN, or other distributed connections are implemented, any of components of the treatment system 900 may be in decentralized locations so that the individual systems 910, 930 and 950 may be physically remote from one other. Alternatively, some or all of the functional features of the diagnostic imaging system 910, the treatment planning system 930, or the treatment delivery system 950 may be integrated with each other within the treatment system 900.

The illustrated treatment delivery system 950 includes a radiation source 952, an imaging system 954, a digital processing system 956, and a treatment couch 958. The radiation source 952, imaging system 954, digital processing system 956, and treatment couch 958 may be coupled to one another via one or more communication channels 960. One example of a treatment delivery system 950 is shown and described in more detail with reference to FIG. 4A.

In one embodiment, the radiation source 952 is a therapeutic or surgical radiation source 952 to administer a prescribed radiation dose to a target volume in conformance with a treatment plan. In one embodiment, the radiation source 952 is the LINAC 203, as described herein. Alternatively, the radiation source 952 may be other types of radiation sources known by those of ordinary skill in the art. For example, the target volume may be an internal organ, a tumor, a region. As described above, reference herein to the target, target volume, target region, target area, or internal target refers to any whole or partial organ, tumor, region, or other delineated volume that is the subject of a treatment plan.

In one embodiment, the imaging system 954 of the treatment delivery system 950 captures intra-treatment images of a patient volume, including the target volume, for registration or correlation with the diagnostic images described above in order to position the patient with respect to the radiation source. Similar to the diagnostic imaging system 910, the imaging system 954 of the treatment delivery system 950 may include one or more sources and one or more detectors.

The treatment delivery system 950 also may include a digital processing system 956 to control the radiation source 952, the imaging system 954, and a treatment couch 958, which is representative of any patient support device. In one embodiment, the treatment couch 958 is the treatment couch 206 coupled to the robotic arm 202 or 302, as described herein. In another embodiment, the treatment couch 958 is the treatment couch coupled to the robotic arm 106, as described herein. Alternatively, other types of patient support devices can be used. In one embodiment, the radiation source 952 is coupled to a first robotic arm (e.g., robotic arm 202), and the treatment couch 958 is coupled to a second robotic arm (e.g., robotic arm 402). The first and second robotic arms may be coupled to the same controller (e.g., controller 201) or to separate controllers. In one embodiment, the first and second robotic arms are identical robotic arms. In one embodiment, the first and second robotic arms each include four rotational DOF and one substantially linear DOF. In another embodiment, the first and second robotic arms each include five rotational DOF and one substantially linear DOF. Alternatively, the first and second robotic arms each include six rotational DOF and one substantially linear DOF. Alternatively, the first and second robotic arms may include dissimilar number and types of DOF. In another embodiment, the first and second robotic arms are dissimilar types of robotic arms. Alternatively, only the first robotic arm is used to move the LINAC 203 with respect to the treatment couch 206.

The digital processing system 956 may include one or more general-purpose processors (e.g., a microprocessor), special purpose processors such as a digital signal processor (DSP), or other devices such as a controller or field programmable gate array (FPGA). Additionally, the digital processing system 956 may include other components (not shown) such as memory, storage devices, network adapters, and the like.

The illustrated treatment delivery system 950 also includes a user interface 962 and a measurement device 964. In one embodiment, the user interface 962 is the user interface 500. In another embodiment, the user interface 962 is the graphical user interface 600. In one embodiment, the user interface 962 allows a user to interface with the treatment delivery system 950. In particular, the user interface 962 may include input and output devices such as a keyboard, a display screen, and so forth. The measurement device 964 may be one or more devices that measure external factors such as the external factors described above, which may influence the radiation that is actually delivered to the target region 20. Some exemplary measurement devices include a thermometer to measure ambient temperature, a hygrometer to measure humidity, a barometer to measure air pressure, or any other type of measurement device to measure an external factor.

In the foregoing specification, embodiments of the invention have been described with reference to specific exemplary embodiments thereof. It will, however, be evident that various modifications and changes may be made thereto without departing from the broader spirit and scope of the present embodiments as set forth in the claims. The specification and drawings are, accordingly, to be regarded in an illustrative rather than a restrictive sense.

What is claimed is:

1. An apparatus, comprising:
a linear accelerator (LINAC); and
a robotic arm coupled to the LINAC, the robotic arm configured to move the LINAC along five degrees of freedom (DOF), wherein the five DOF comprise four rotational DOF and one substantially linear DOF, wherein the substantially linear DOF is a substantially vertical, linear DOF having a substantially linear axis for translational movements of the LINAC along a substantially vertical line in the z-axis substantially perpendicular to the mutually orthogonal horizontal coordinate x- and y-axes, and wherein the robotic arm comprises:
a wrist assembly rotatably mounted to a mounting plate;
an elbow assembly coupled to the wrist assembly, the elbow assembly comprising one or more elbow gearboxes;
a shoulder assembly coupled to the elbow assembly, the shoulder assembly comprising one or more shoulder gearboxes; and
a track and a track mount assembly coupled to the shoulder assembly to provide the substantially linear axis and configured to support a load of the LINAC up to 500 lbs while enabling movement of the robotic arm using smaller gearboxes than capable without the track and track mount assembly.

2. The apparatus of claim 1, wherein the four rotational DOF comprise:
one rotational axes for translational movement of the LINAC along mutually orthogonal horizontal coordinate x- and y-axes; and
three rotational axes for roll-, pitch-, and yaw- rotational movements about an x-axis, a y-axis, and a z-axis, respectively.

3. The apparatus of claim 1, wherein the substantially linear DOF is a first DOF of the five DOF, and wherein the first DOF is configured to move the other four rotational DOF of the robotic arm.

4. The apparatus of claim 3, wherein the first DOF is the DOF closest to the base end of the robotic arm.

5. The apparatus of claim 3, wherein the first DOF is configured to move the LINAC along the substantially linear axis throughout substantially an entire range of motion of the LINAC without movement of the LINAC along the four rotational DOF.

6. The apparatus of claim 1, wherein the robotic arm is configured to move the LINAC along six DOF, and wherein the six DOF comprise:
  five rotational DOF; and
  one substantially linear DOF.

7. The apparatus of claim 6, wherein the five rotational DOF comprise:
  two rotational axes for translational movements of the LINAC along mutually orthogonal horizontal coordinate x- and y-axes; and
  three rotational axes for roll-, pitch-, and yaw- rotational movements about the x-axis, the y-axis, and a z-axis, respectively.

8. The apparatus of claim 6, wherein the substantially linear DOF is a first DOF of the six DOF, and wherein the first DOF is configured to move the other five rotational DOF of the robotic arm.

9. The apparatus of claim 8, wherein the first DOF is configured to move the LINAC along the substantially linear axis throughout substantially an entire range of motion of the LINAC without movement of the LINAC along the five rotational DOF.

10. The apparatus of claim 1, wherein the track is vertically oriented.

11. The apparatus of claim 10, wherein the track is coupled to a vertical side of a column.

12. The apparatus of claim 11, wherein the column is mounted to at least one of a floor and a ceiling.

13. The apparatus of claim 10, wherein the track is coupled to a wall.

14. The apparatus of claim 1, wherein the track is horizontally oriented.

15. The apparatus of claim 14, wherein the track is mounted to at least one of a floor and a ceiling.

16. The apparatus of claim 1, wherein the wrist assembly comprises:
  a tool-yaw joint coupled to the mounting plate;
  a tool-pitch joint coupled to the tool-yaw joint; and
  a tool-roll joint coupled to the tool-pitch joint.

17. The apparatus of claim 16, wherein the tool-yaw joint is coupled to rotate the LINAC along a z-axis, wherein the tool-pitch joint is coupled to rotate the LINAC along a y-axis, and wherein the tool-roll joint is coupled to rotate the LINAC along a x-axis.

18. The apparatus of claim 17, wherein the elbow assembly comprises: a first drive shaft coupled to the tool-yaw joint;
  a first motor coupled to the first drive shaft, the first motor configured to drive rotational movement of the tool-yaw joint of the robotic arm in a first rotational axis of the six DOF of the robotic arm;
  a second drive shaft coupled to the tool-pitch joint;
  a second motor coupled to the second drive shaft, the second motor configured to drive rotational movement of the tool-pitch joint of the robotic arm in a second rotational axis of the six DOF of the robotic arm;
  a third drive shaft coupled to the tool-roll joint; and
  a third motor coupled to the third drive shaft, the third motor configured to drive rotational movement of the tool-roll joint of the robotic arm in a third rotational axis of the six DOF of the robotic arm.

19. The apparatus of claim 18, further comprising:
  an elbow joint coupled to the elbow assembly and the shoulder assembly, wherein the elbow joint comprises the elbow gearbox configured to drive rotational movement of elbow assembly of the robotic arm in a fourth rotational axis of the six DOF of the robotic arm; and
  a shoulder joint coupled to the shoulder assembly and the track mount assembly, wherein the shoulder joint comprises a the shoulder gearbox configured to drive rotational movement of the robotic arm in a fifth rotational axis of the six DOF of the robotic arm.

20. The apparatus of claim 19, wherein the elbow and shoulder gearboxes are configured to move the LINAC in a two-dimensional horizontal plane.

21. The apparatus of claim 20, wherein the track and track assembly are configured to move the LINAC in a substantially linear translational movement either in the two-dimensional horizontal plane or perpendicular to the two-dimensional horizontal plane.

22. The apparatus of claim 18, wherein the robotic arm is configured to move the LINAC along seven DOF, and wherein the seven DOF comprise:
  six rotational DOF; and
  one substantially linear DOF.

23. The apparatus of claim 22, wherein the six rotational DOF comprise:
  three rotational axes for translations along mutually orthogonal x-, y-, and z-coordinate axes; and
  three rotational axes for roll-, pitch-, and yaw- rotations about x-, y-, and z- axes, respectively, and wherein the one substantially linear DOF is a substantially linear DOF that includes a substantially linear axis for translational movement of the LINAC along either a substantially vertical line in the z-axis substantially perpendicular to the mutually orthogonal horizontal coordinate x- and y-axes or a substantially horizontal line in the mutually orthogonal horizontal coordinate x- and y-axes substantially perpendicular to the z-axis.

24. The apparatus of claim 23, further comprising:
  a plate member rotatably mounted on the track mount assembly and the shoulder assembly;
  a first shoulder joint coupled to the shoulder assembly and the plate member, wherein the first shoulder joint comprises a first shoulder gearbox configured to drive a fifth rotational axis of the six DOF of the robotic arm; and
  a second shoulder joint coupled to the plate member and the track mount assembly, wherein the second shoulder joint comprises a second shoulder gearbox configured to drive an sixth rotation axis of the six DOF of the robotic arm.

25. The apparatus of claim 1, further comprising:
  a mounting plate coupled to the LINAC;
  a wrist assembly of the robotic arm coupled to the mounting plate, the mounting plate coupled to the LINAC; and
  a track mount assembly coupled to a track, wherein the track mount assembly including a track mount collar.

26. The apparatus of claim 1, further comprising a controller coupled to the robotic arm, wherein the controller is configured to move the robotic arm and the LINAC in the five DOF.

27. The apparatus of claim 26, further comprising a user interface unit coupled to the controller, wherein the user interface unit is configured to manually move the robotic arm and the LINAC in the five DOF.

28. A method, comprising:
providing a linear accelerator (LINAC) coupled to a robotic arm; and
moving the LINAC along five degrees of freedom (DOF), wherein the five DOF comprise four rotational DOF and one substantially linear DOF, wherein the substantially linear DOF is a substantially vertical, linear DOF having a substantially linear axis for translational movements of the LINAC along a substantially vertical line in the z-axis substantially perpendicular to the mutually orthogonal horizontal coordinate x- and y-axes, and wherein the robotic arm comprises:
a wrist assembly rotatably mounted to a mounting plate;
an elbow assembly coupled to the wrist assembly, the elbow assembly comprising one or more elbow gearboxes;
a shoulder assembly coupled to the elbow assembly, the shoulder assembly comprising one or more shoulder gearboxes; and
a track and a track mount assembly coupled to the shoulder assembly to provide the substantially linear axis and configured to support a load of the LINAC up to 500 lbs while enabling movement of the robotic arm using smaller gearboxes than capable without the track and track mount assembly.

29. The method of claim 28, wherein moving the LINAC along the four rotational DOF comprises:
moving the LINAC in one rotational axis for translational movement of the LINAC along mutually orthogonal horizontal coordinate x- and y-axes; and
moving the LINAC in three rotational axes for roll-, pitch-, and yaw-rotational movements about an x-axis, a y-axis, and a z-axis, respectively.

30. The method of claim 28, further comprising moving the LINAC along the substantially linear axis throughout substantially an entire range of motion of the LINAC without moving the LINAC along the four rotational DOF.

31. The method of claim 28, wherein moving the LINAC along five DOF comprises:
rotating the LINAC along the z-axis using a tool-yaw joint of the robotic arm;
rotating the LINAC along the y-axis using a tool-pitch joint of the robotic arm;
rotating the LINAC along the x-axis using a tool-roll joint of the robotic arm;
rotating the LINAC along the one horizontal rotational axis using a elbow joint of the robotic arm; and
translating the LINAC along a substantially linear axis using a track and track mount assembly either in one horizontal rotational axis or perpendicular to the one horizontal rotational axis.

32. The method of claim 28, further comprising moving the LINAC along a sixth DOF, wherein the sixth DOF comprises an additional rotational DOF.

33. The method of claim 32, wherein moving the LINAC along the six DOF comprises:
moving the LINAC in two rotational axes for translational movement of the LINAC along mutually orthogonal horizontal coordinate x- and y-axes; and
moving the LINAC in three rotational axes for roll-, pitch-, and yaw-rotational movements about an x-axis, a y-axis, and a z-axis, respectively.

34. The method of claim 33, wherein moving the LINAC along the one substantially linear DOF comprises moving the LINAC along a substantially horizontal, linear DOF having a substantially linear axis for translational movements of the LINAC along a horizontal line in the mutually orthogonal horizontal coordinate x- and y-axes that is perpendicular to the z-axis.

35. The method of claim 32, further comprising moving the LINAC along the substantially linear axis throughout substantially an entire range of motion of the LINAC without moving the LINAC along the five rotational DOF.

36. The method of claim 32, wherein moving the LINAC further comprises:
rotating the LINAC along the z-axis using a tool-yaw joint of the robotic arm;
rotating the LINAC along the y-axis using a tool-pitch joint of the robotic arm;
rotating the LINAC along the x-axis using a tool-roll joint of the robotic arm;
rotating the LINAC along the two horizontal rotational axes using a elbow joint and a shoulder joint of the robotic arm; and
translating the LINAC along a substantially linear axis using a track and track mount assembly perpendicular to the two horizontal rotational axes.

37. The method of claim 28, further comprising rotating the LINAC along an additional translational axis using an additional shoulder joint.

38. A system, comprising:
a linear accelerator (LINAC);
a first robotic arm coupled to the LINAC, the robotic arm configured to move the LINAC along five degrees of freedom (DOF), wherein the five DOF comprise four rotational DOF and one substantially linear DOF;
a treatment couch; and
a second robotic arm coupled to the treatment couch, the second robotic arm is configured to move the treatment couch along five degrees of freedom (DOF), wherein the five DOF comprise four rotational DOF and one substantially linear DOF, wherein the substantially linear DOF is a substantially vertical, linear DOF having a substantially linear axis for translational movements of the LINAC along a substantially vertical line in the z-axis substantially perpendicular to the mutually orthogonal horizontal coordinate x- and y-axes, and wherein the first robotic arm comprises:
a wrist assembly rotatably mounted to a mounting plate;
an elbow assembly coupled to the wrist assembly, the elbow assembly comprising one or more elbow gearboxes;
a shoulder assembly coupled to the elbow assembly, the shoulder assembly comprising one or more shoulder gearboxes; and
a track and a track mount assembly coupled to the shoulder assembly to provide the substantially linear axis and configured to support a load of the LINAC up to 500 lbs while enabling movement of the first robotic arm using smaller gearboxes than capable without the track and track mount assembly.

39. The system of claim 38, further comprising a controller coupled to the first and second robotic arms, wherein the controller is configured to control movement of the LINAC, the treatment couch, or both the LINAC and the treatment couch to align a radiation source of the LINAC with a treatment target within a patient disposed on the treatment couch.

40. The system of claim 39, wherein the orientation and position of the treatment couch and the LINAC are dynamically coordinated by the controller.

41. The system of claim 39, further comprising an imaging system coupled to the controller to generate a plurality of images of the patient.

42. The system of claim 39, wherein the controller is configured to positioning the treatment couch and the LINAC to access a treatment target in a previously obstructed location caused by a positioning restriction within a mechanical range of motion of the first robotic arm and the LINAC.

43. The system of claim 42, wherein the positioning restriction comprises at least one of obstructions of a possible collision between at least two of the first robotic arm, the second robotic arm, the LINAC, and the treatment couch.

44. The system of claim 42, wherein positioning restriction comprises obstructions of a radiation beam of the LINAC with at least one of the treatment couch, the first robotic arm, or the second robotic arm.

45. The system of claim 38, wherein the first robotic arm and the second robotic arm are substantially identical.

46. A method comprising:
providing a LINAC coupled to a first robotic arm;
providing a treatment couch coupled to a second robotic arm;
moving the LINAC along five degrees of freedom (DOF) using the first robotic arm, wherein the five DOF of the first robotic arm comprise four rotational DOF and one substantially linear DOF, wherein the substantially linear DOF is a substantially vertical, linear DOF having a substantially linear axis for translational movements of the LINAC along a substantially vertical line in the z-axis substantially perpendicular to the mutually orthogonal horizontal coordinate x- and y-axes, and wherein the robotic arm comprises:
a wrist assembly rotatably mounted to a mounting plate;
an elbow assembly coupled to the wrist assembly, the elbow assembly comprising one or more elbow gearboxes;
a shoulder assembly coupled to the elbow assembly, the shoulder assembly comprising one or more shoulder gearboxes; and
a track and a track mount assembly coupled to the shoulder assembly to provide the substantially linear axis and configured to support a load of the LINAC up to 500 lbs while enabling movement of the first robotic arm using smaller gearboxes than capable without the track and track mount assembly; and
moving the treatment couch along five DOF using the second robotic arm, wherein the five DOF of the second robotic arm comprise four rotational DOF and one substantially linear DOF.

47. The method of claim 46, wherein moving the LINAC along five DOF comprises: rotating the LINAC along the z-axis using a tool-yaw joint of the first robotic arm;
rotating the LINAC along the y-axis using a tool-pitch joint of the first robotic arm;
rotating the LINAC along the x-axis using a tool-roll joint of the first robotic arm;
rotating the LINAC along the one horizontal rotational axis using a elbow joint of the first robotic arm; and
translating the LINAC along a substantially linear axis using a first track and a first track mount assembly in the vertical linear axis perpendicular to the horizontal linear axis, and wherein moving the treatment couch along five DOF comprises:
rotating the treatment couch along the z-axis using a tool-yaw joint of the second robotic arm;
rotating the treatment couch along the y-axis using a tool-pitch joint of the second robotic arm;
rotating the treatment couch along the x-axis using a tool-roll joint of the second robotic arm;
rotating the treatment couch along the one horizontal rotational axis using a elbow joint of the second robotic arm; and
translating the treatment couch along a substantially linear axis using a second track and a second track mount assembly either in a horizontal axis or a vertical axis.

48. The method of claim 46, further comprising:
moving the LINAC along a sixth DOF using the first robotic arm, wherein the sixth DOF of the first robotic arm comprises an additional rotational DOF; and
moving the treatment couch along a sixth DOF using the second robotic arm, wherein the sixth DOF of the second robotic arm comprises an additional rotational DOF.

49. The method of claim 46, further comprising dynamically coordinating orientations and positions of the LINAC and the treatment couch.

50. The method of claim 49, wherein dynamically coordinating the orientations and positions of the LINAC and the treatment couch comprise aligning a radiation source of the LINAC with a treatment target within a patient disposed on the treatment couch.

51. The method of claim 49, wherein dynamically coordinating the orientations and positions of the L1NAC and the treatment couch comprise positioning the LINAC and the treatment couch to access a treatment target in a previously obstructed location caused by a positioning restriction within a mechanical range of motion of the first robotic arm and the LINAC.

52. The method of claim 50, wherein the positioning restriction comprise obstructions of a radiation source of the LINAC due to at least one of an x-ray imaging source and detector, the first robotic arm, the second robotic arm, or the treatment couch.

53. The method of claim 46, further comprising:
providing an imaging system having an imaging field of view; and
maintaining the LINAC substantially outside of the imaging field of view for all supported treatment positions.

* * * * *